(12) United States Patent
Copa et al.

(10) Patent No.: US 8,764,775 B2
(45) Date of Patent: Jul. 1, 2014

(54) ANASTOMOSIS DEVICE AND RELATED METHODS

(75) Inventors: Vincent G. Copa, Minnetonka, MN (US); Kory P. Hamel, Bloomington, MN (US); Hans A. Mische, St. Cloud, MN (US)

(73) Assignee: AMS Research Corporation, Minnetonka, MN (US)

( * ) Notice: Subject to any disclaimer, the term of this patent is extended or adjusted under 35 U.S.C. 154(b) by 1584 days.

(21) Appl. No.: 10/919,775

(22) Filed: Aug. 16, 2004

(65) Prior Publication Data

US 2005/0131431 A1 Jun. 16, 2005

Related U.S. Application Data

(63) Continuation-in-part of application No. 10/646,383, filed on Aug. 21, 2003.

(60) Provisional application No. 60/405,140, filed on Aug. 22, 2002.

(51) Int. Cl.
*A61B 17/11* (2006.01)

(52) U.S. Cl.
USPC .......................................................... 606/153

(58) Field of Classification Search
USPC ...................... 606/153, 215, 216; 604/164.03
See application file for complete search history.

(56) References Cited

U.S. PATENT DOCUMENTS

| 4,701,162 | A | 10/1987 | Rosenberg |
| 4,705,502 | A | 11/1987 | Patel |
| 4,792,330 | A | 12/1988 | Lazarus et al. |
| 4,848,367 | A | 7/1989 | Avant et al. |
| 4,873,977 | A | 10/1989 | Avant et al. |
| 4,909,785 | A | 3/1990 | Burton et al. |
| 4,911,164 | A | 3/1990 | Roth |
| 4,932,956 | A | 6/1990 | Reddy et al. |
| 5,047,039 | A | 9/1991 | Avant et al. |
| 5,123,908 | A | 6/1992 | Chen |
| 5,152,772 | A | 10/1992 | Sewell, Jr. |
| 5,306,226 | A | 4/1994 | Salama |
| 5,540,701 | A | 7/1996 | Sharkey et al. |
| 5,545,171 | A | 8/1996 | Sharkey et al. |
| 5,695,504 | A | 12/1997 | Gifford, III et al. |
| 5,707,380 | A | 1/1998 | Hinchliffe et al. |

(Continued)

FOREIGN PATENT DOCUMENTS

| WO | WO 92/04869 | 4/1992 |
| WO | WO 96/07447 | 3/1996 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Katherine Dowe
(74) *Attorney, Agent, or Firm* — Kagan Binder, PLLC

(57) ABSTRACT

Described are methods and devices relating to reconnecting the urethra and bladder after a radical prostatectomy, wherein the devices incorporate tissue approximating structure to maintain contact between a severed bladder neck tissue and a severed urethral stump tissue, preferably without the use of sutures.

19 Claims, 26 Drawing Sheets

(56) References Cited

U.S. PATENT DOCUMENTS

| | | | |
|---|---|---|---|
| 5,833,698 | A | 11/1998 | Hinchliffe et al. |
| 5,931,842 | A | 8/1999 | Goldsteen et al. |
| 5,964,791 | A | 10/1999 | Bolmsjo |
| 6,024,748 | A | 2/2000 | Manzo et al. |
| 6,119,045 | A | 9/2000 | Bolmsjo |
| 6,149,667 | A | 11/2000 | Hovland et al. |
| 6,193,734 | B1 | 2/2001 | Bolduc et al. |
| 6,238,368 | B1 | 5/2001 | Devonec |
| 6,254,570 | B1 | 7/2001 | Rutner et al. |
| 6,299,598 | B1 * | 10/2001 | Bander ............... 604/101.03 |
| 6,302,905 | B1 | 10/2001 | Goldsteen et al. |
| 6,391,039 | B1 | 5/2002 | Nicholas et al. |
| 6,416,545 | B1 | 7/2002 | Mikus et al. |
| 6,440,146 | B2 | 8/2002 | Nicholas et al. |
| 6,447,533 | B1 | 9/2002 | Adams |
| 6,461,367 | B1 | 10/2002 | Kirsch et al. |
| 6,485,496 | B1 | 11/2002 | Suyker et al. |
| 6,494,908 | B1 | 12/2002 | Huxel et al. |
| 6,520,974 | B2 | 2/2003 | Tanner et al. |
| 6,530,932 | B1 | 3/2003 | Swayze et al. |
| 6,562,024 | B2 | 5/2003 | Alvarez de Toledo et al. |
| 6,565,579 | B2 | 5/2003 | Kirsch et al. |
| 6,599,311 | B1 | 7/2003 | Biggs et al. |
| 6,602,243 | B2 | 8/2003 | Noda |
| 6,695,832 | B2 | 2/2004 | Schon et al. |
| 6,702,825 | B2 | 3/2004 | Frazier et al. |
| 6,719,709 | B2 | 4/2004 | Whalen et al. |
| 6,719,749 | B1 | 4/2004 | Schweikert et al. |
| 6,726,697 | B2 | 4/2004 | Nicholas et al. |
| 6,740,098 | B2 | 5/2004 | Abrams et al. |
| 6,746,456 | B2 | 6/2004 | Xiao |
| 6,746,472 | B2 | 6/2004 | Frazier et al. |
| 6,821,283 | B2 * | 11/2004 | Barzell et al. ............... 606/144 |
| 2002/0002363 | A1 | 1/2002 | Urakawa et al. |
| 2002/0087176 | A1 | 7/2002 | Greenhalgh |
| 2002/0143302 | A1 * | 10/2002 | Hinchliffe et al. ........... 604/272 |
| 2003/0069629 | A1 | 4/2003 | Jadhav et al. |
| 2003/0208183 | A1 | 11/2003 | Whalen et al. |
| 2003/0229364 | A1 * | 12/2003 | Seiba ............... 606/153 |
| 2004/0078047 | A1 | 4/2004 | Nicholas et al. |
| 2004/0087995 | A1 | 5/2004 | Copa et al. |
| 2005/0192602 | A1 * | 9/2005 | Manzo ............... 606/153 |
| 2005/0251155 | A1 * | 11/2005 | Orban, III ............... 606/153 |

FOREIGN PATENT DOCUMENTS

| | | |
|---|---|---|
| WO | WO 99/16359 | 4/1999 |
| WO | WO 99/21490 | 5/1999 |
| WO | WO 99/21491 | 5/1999 |
| WO | WO 9921491 A1 * | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

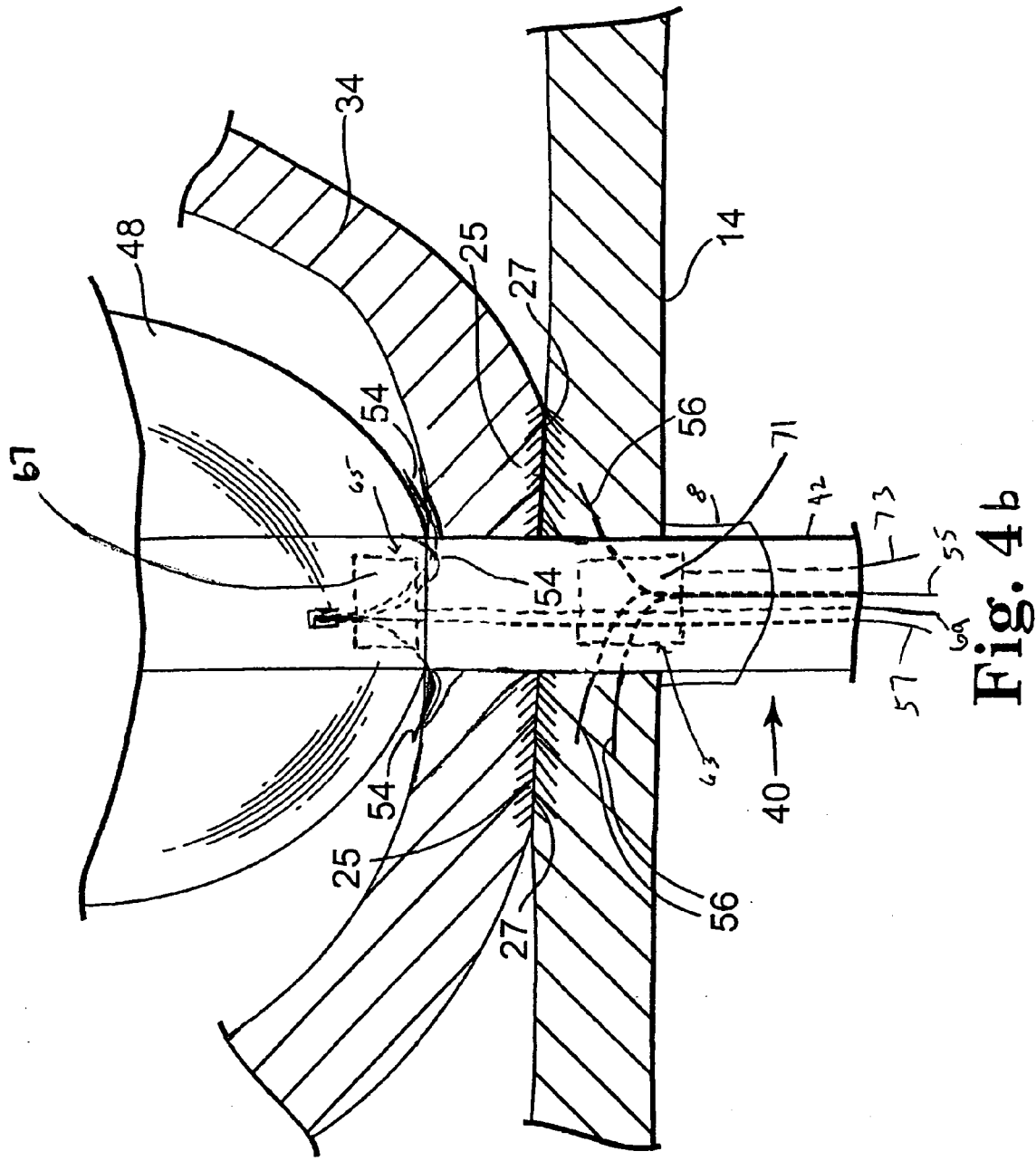

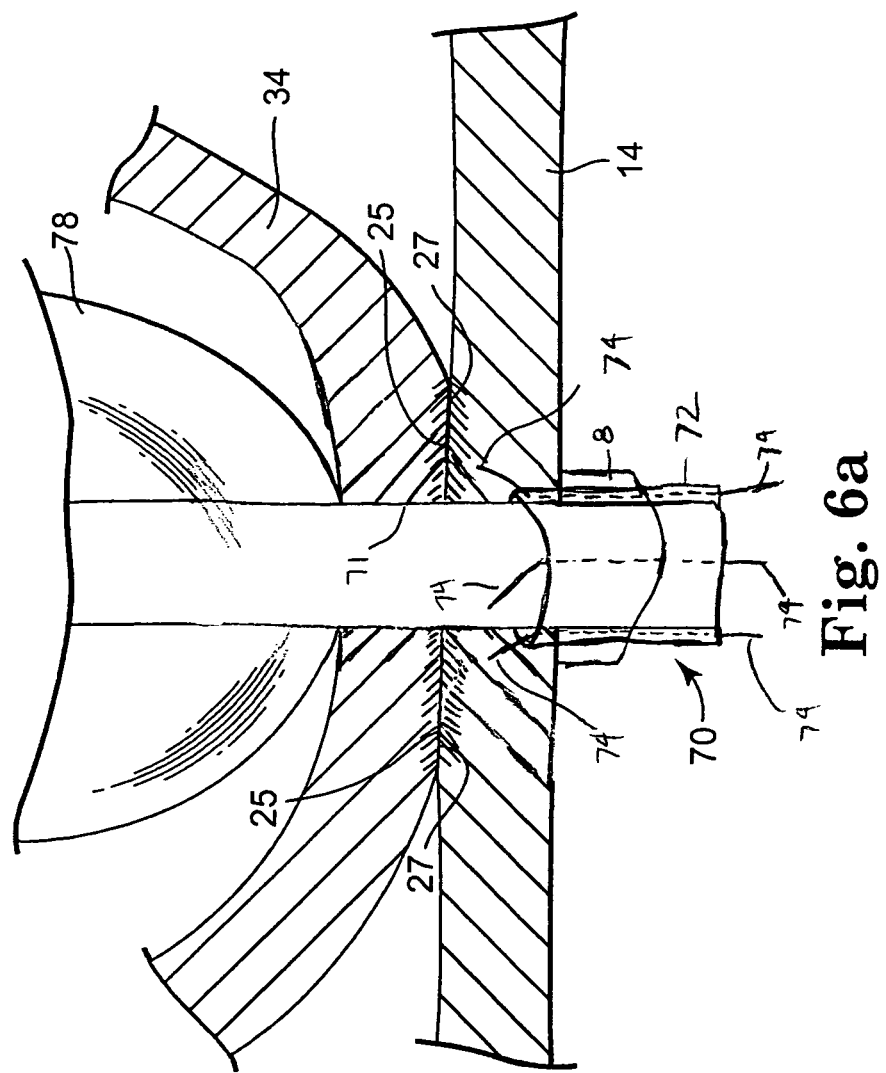

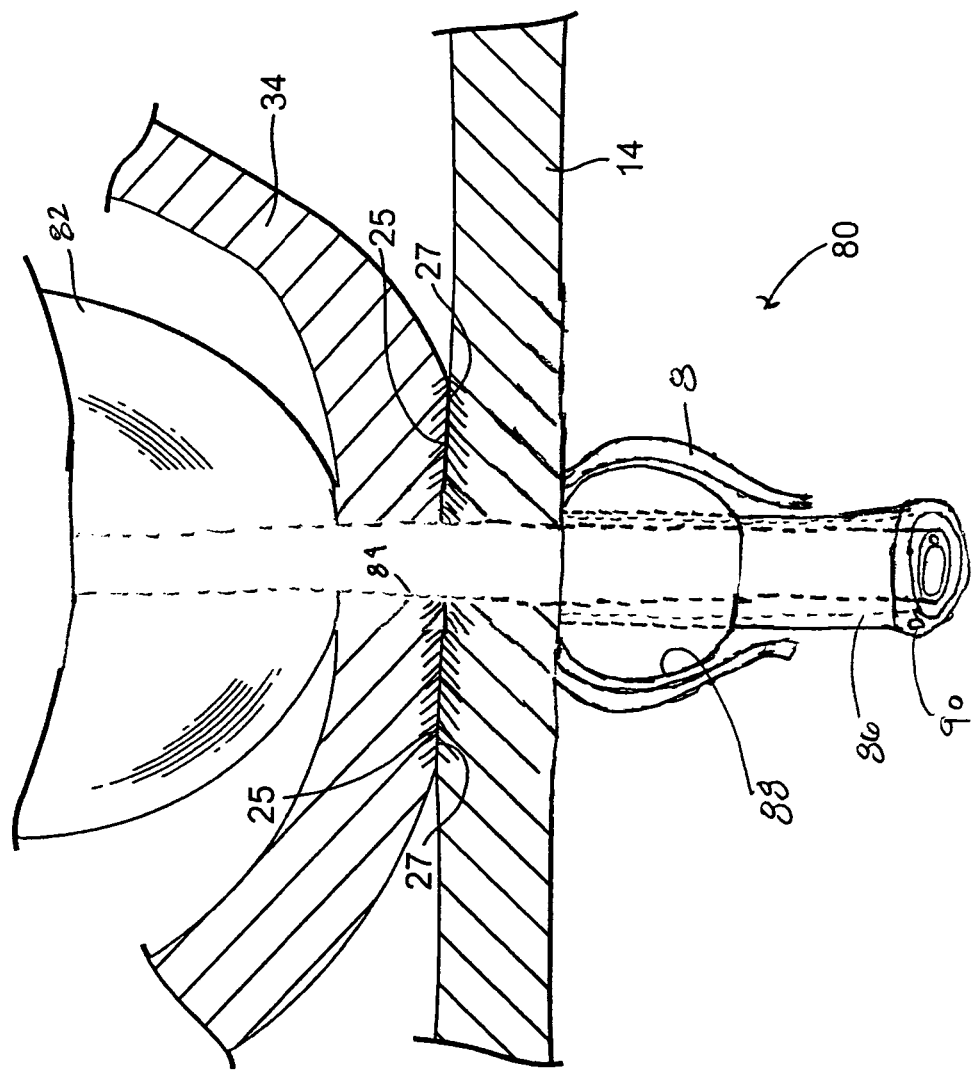

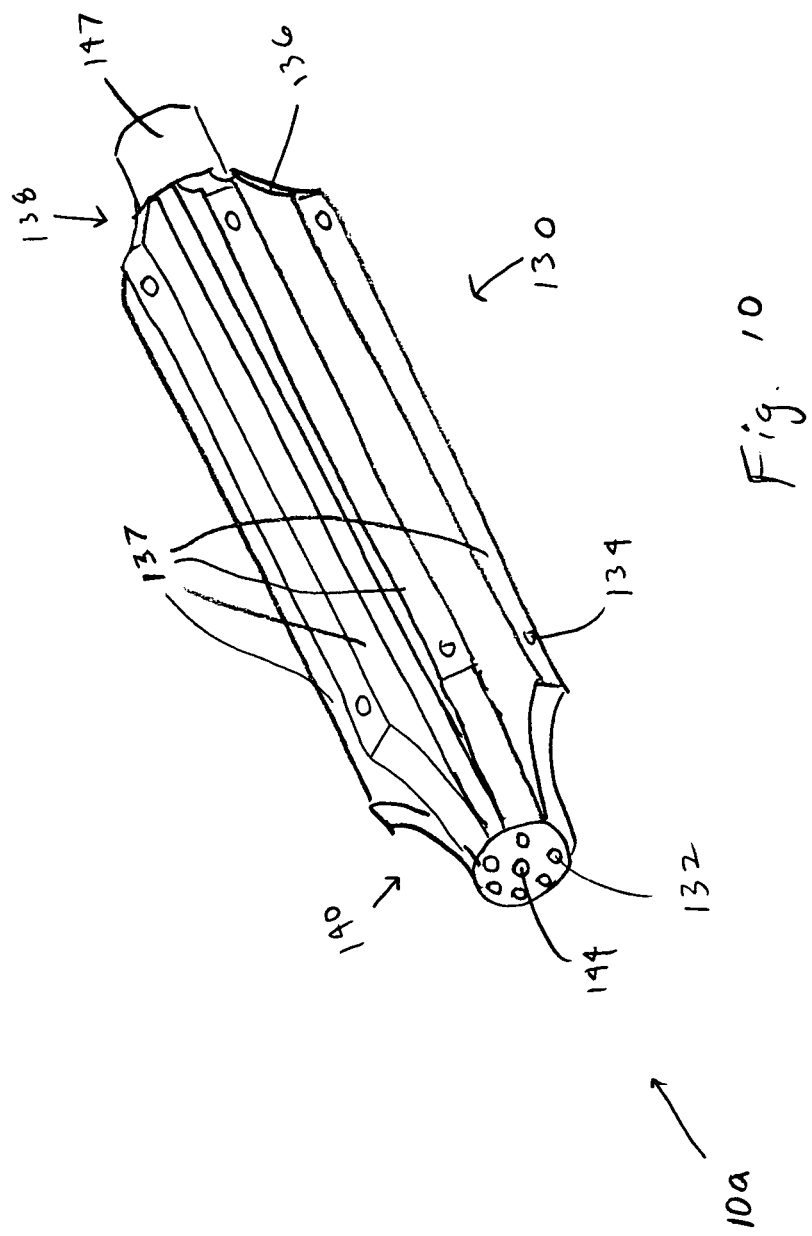

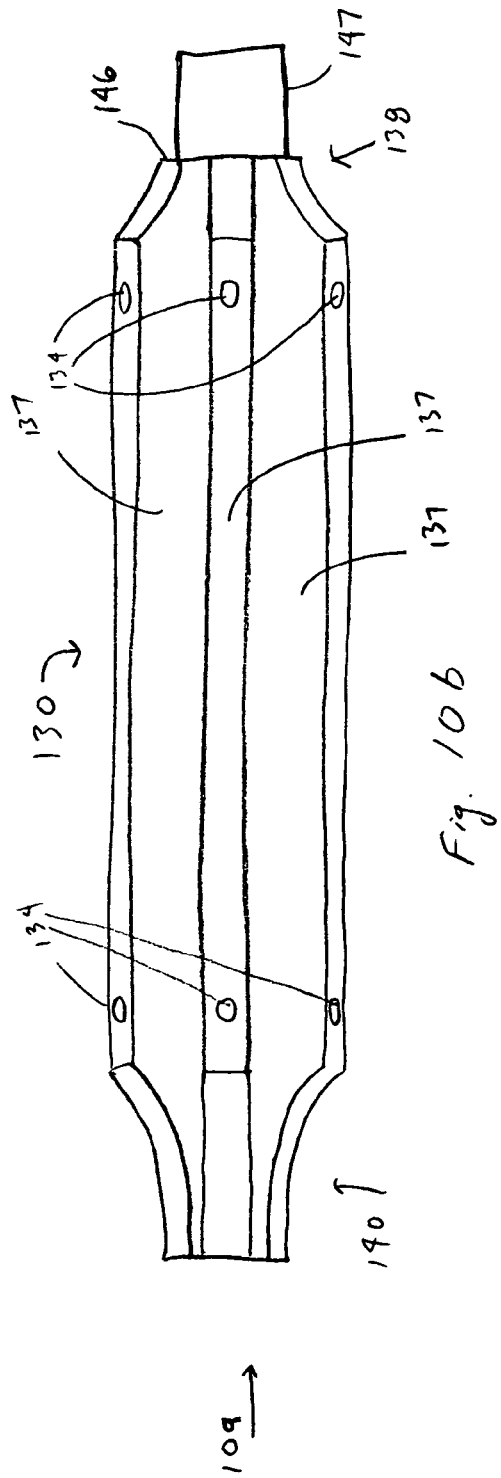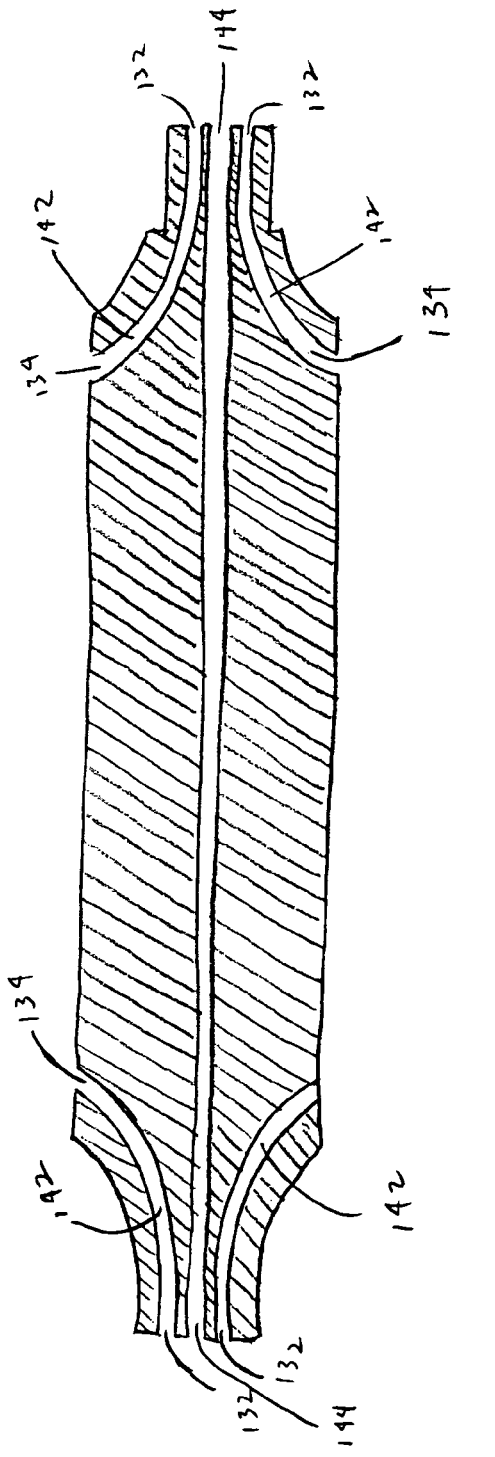

ANASTOMOSIS DEVICE AND RELATED METHODS

CROSS REFERENCE TO RELATED APPLICATION

The present application is a continuation in part of U.S. Ser. No. 10/646,383, filed Aug. 21, 2003, which is the nonprovisional application claiming priority to Provisional Application Ser. No. 60/405,140, filed Aug. 22, 2002, the entire contents of each of which are fully incorporated herein by reference.

FIELD OF THE INVENTION

The invention generally relates to methods of performing anastomosis procedures, including urethral procedures that involve reconnecting urethra and bladder tissues after a radical prostatectomy, as well as related devices. Certain particular embodiments of the invention relate to methods and devices for performing a vesico-urethral anastomosis and end-to-end urethral anastomosis.

BACKGROUND

In a radical prostatectomy, the surgeon removes all or most of a patient's prostate. Because the urethra travels through the prostate immediately before reaching the bladder, the upper part of the urethra is removed in the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these anatomical bodies. Installation of sutures, however, with a needle, to connect the severed tissues, can be a difficult and often technique-sensitive task. Many factors can make this task difficult, including a very small amount of tissue to work with (at the urethral stump and at the bladder neck), proximal ureters at the bladder, and a proximal nerve bundle and sphincter at the urethral stump. These factors result in a complicated and delicate suturing procedure that, if not performed properly, could result in complications such as leakage, difficulty in healing or failure to heal, incontinence, or impotence. Specific problems include necrosis of the sutured tissues; stricture of the urethra, which impedes the flow of fluid through it; and a urethra-bladder connection that is not fluid-tight. In addition, methods of suturing the urethra to the bladder allow for accidental or inadvertent piercing of the nearby neurovascular bundle, which can cause incontinence or impotence.

SUMMARY

The invention relates to anastomosis devices that include tissue approximating structure, wherein the tissue approximating structure is positionable along a length of the device.

Anastomosis devices that include tissue approximating structure are described in Applicants' co-pending U.S. patent application Ser. No. 10/646,383, filed Aug. 21, 2003, entitled "ANASTOMOSIS DEVICE AND RELATED METHODS," the entirety of which is incorporated herein by reference. These devices allow for methods of re-connecting tissue with the use of the tissue approximating structure.

Advantageously, anastomosis devices that include tissue approximating structure avoid the need for sutures to connect severed tissue, in anastomosis procedures. The ability to avoid sutures provides very significant advantages of avoiding the potential for damage to surrounding tissues and nerves that can be caused by installation of sutures using a needle. Such damage can include, for example in certain urethral anastomosis processes, damage to ureters at the bladder or damage to the sphincter or nerves located in the perineal floor. Damage to any of these tissues has the potential to cause incontinence or impotence. Additionally, installing sutures is a difficult and technique-sensitive process that must be performed in a confined space and that would be avoided if possible based on other alternatives. Thus, the invention offers the very significant advantage of eliminating the need to use sutures to re-attach severed tissues, and, during urethral anastomosis, the attendant potential damage to those sensitive proximal tissues and nerves and the possibility of incontinence or impotence.

As additional advantage, the inventive methods and devices, by eliminating sutures, can significantly reduce the amount of time required to perform certain anastomosis procedures. For example, the amount of time for suture installation during a vesico-urethral anastomosis can be in the range of from 20 to 30 minutes up to an hour. A suturing step of a retropubic procedure, for example, may take 20 or 30 minutes, or up to an hour for a laparoscopic procedure. These amounts of time may be significantly reduced, according to the invention, due to the elimination of a suturing step. Reduced procedure time also results in the attendant advantages of reduced patient time under anesthesia, which can reduce the costs and complications caused by anesthesia, as well as related general costs.

According to the invention, an anastomosis device can include positionable tissue approximating structure, e.g., tissue approximating structure, that can be moved along a length of the device, for positioning as desired in a particular procedure. A positionable tissue approximating structure can allow for precise control of the location of tissue approximating structure, in a delicate anastomosis procedure. During an anastomosis procedure, after the anastomosis device and approximating structure are located as desired, the tissue approximating structure can be used to cause or maintain contact between severed portions of tissue to allow or cause the severed tissue surfaces to heal together, instead of using sutures.

A device of the invention may be used, for example, in performing procedures such as a vesico-urethral anastomosis in association with a radical prostatectomy, with an end-to-end urethral anastomosis, or with other anastomosis procedures that will be understood and appreciated based on the present description. According to certain specific embodiments, a device can include positionable tissue approximating structure such as a positionable balloon or positionable tines, in combination with certain common features of a urethral (e.g., Foley) catheter. The device can be used during a urethral anastomosis procedure to produce or maintain contact between tissues for healing, and may thereafter optionally be left installed during the healing process to function to allow the tissue to heal, while at the same time functioning as a urethral catheter, e.g., to drain urine from the bladder.

Embodiments of anastomosis devices of the invention can include one or more (e.g., one or two) positionable tissue approximating structures, such as one or multiple sets of opposing tines or one or more balloons, any of which can be positionable, and any of which may optionally be fixed in position along the length of the anastomosis device. Certain specific combinations may include a fixed balloon and a moveable balloon or a fixed set of tines and a positionable set of tines. A positionable tissue approximating structure may be located internal to an elongate body of an anastomosis device, where the approximating structure may be moved within the hollow interior. In other embodiments, a positionable tissue approximating structure may be located external to the elongate body, e.g., in a second (outer) elongate body located around the first elongate body where the outer body can slide along a length of the first (inner) elongate body to allow positioning of the tissue approximating structure along a length of the inner elongate body.

According to certain embodiments of anastomosis devices of the invention, wherein a positionable tissue approximating structure includes tines located within a hollow interior of an elongate body, the positionable tissue approximating structure may include a tine assembly and a tine support, the two of which can work together to position and actuate the tine assembly for tissue approximation. The positionable tissue approximating structure, e.g., as part of the tine support, may optionally include guide structure that aligns the tine support inside of the elongate body and inhibits undesired movement of the tine support, e.g., inhibits rotational movement of the tine support about the longitudinal axis of the tine support.

Preferred positionable tissue approximating structure may be remotely positionable and actuatable by the use of positioning and actuating mechanisms that are at a convenient location, such as at a proximal end of an anastomosis device. Accordingly, such embodiments of positionable tissue approximating structure can be positioned, actuated, and adjusted, remotely (e.g., using positioning and actuating mechanisms at the proximal end of the device) during a surgical procedure. The device, overall, thus allows a surgeon to position and re-position a tissue approximating structure during a procedure to effect optimal positioning of the tissue approximating structure and of tissue.

Certain embodiments of anastomosis devices of the invention, in addition to tissue approximating structure, can include features and structures that allow the device to function as a catheter, e.g., a urethral catheter, to drain the bladder. Such features of a catheter can include, for example, a drain lumen, a balloon, an inflation lumen, etc., such that the anastomosis device can perform both the functions of an anastomosis device and a catheter.

Methods of the invention can use an anastomosis device as described herein, including positionable tissue approximating structure. Certain methods use anastomosis devices that also include features of a catheter. A device of the invention can be used to facilitate healing during anastomosis, without sutures, and optionally with draining of the bladder with a single anastomosis device.

According to specific methods, an anastomosis device that includes features of a catheter can be installed during or after a radical prostate removal procedure, and can remain installed with the bladder-draining function and the tissue-approximating function in effect until the anastomosis is completely healed and severed tissues, e.g., bladder and urethra, are re-connected. Thus, an advantage associated with certain specific embodiments of inventive methods and devices can be that an anastomosis device performs dual functions when installed during and following an anastomosis procedure, of draining the bladder and functioning as a tissue approximating structure, at the same time.

According to the present description, the term "distal end" refers to a portion of an anastomosis device that is inserted into a body lumen during an anastomosis procedure such as tissue in the region of a bladder, urethra, urethral stump, or perineal wall. The term "proximal end" refers to a portion of an anastomosis device that is opposite from the distal end, including a portion that remains exterior to the body during use.

The terms "tissue approximating" and simply "approximating" refer to a process of bringing or holding body tissues in contact for healing. Examples include: the process of bringing severed surfaces of a bladder neck and a urethral stump, or two opposing severed urethral tissues, into contact for healing; and the process of holding severed surfaces of a bladder neck and a urethral stump, or two opposing severed urethral tissues, together for healing.

An aspect of the invention relates to an anastomosis device. The device includes an elongate body and positionable tissue approximating structure that can be positioned length-wise along the elongate body and that can extend from the device over a range of positions along a length of the elongate body to contact tissue for anastomosis.

Another aspect of the invention relates to an anastomosis device that includes an elongate body having a body wall having an interior surface, positionable tissue approximating structure within the elongate body that can be moved length-wise within the elongate body, the positionable tissue approximating structure comprising a tine and a tine support. The interior surface of the body wall includes guide structure along a length of the interior surface to guide the positionable tissue approximating structure along an interior length of the elongate body. The tine support includes a surface feature corresponding to the guide structure of the interior surface such that the tine support is inhibited from rotational movement within the elongate body.

Still another aspect of the invention relates to a method of performing anastomosis. The method includes inserting a portion of an anastomosis device into a body lumen, wherein the anastomosis device includes an elongate body having a proximal end and a distal end, and positionable tissue approximating structure that can be positioned length-wise relative to the elongate body; moving the positionable tissue approximating structure along a length of the elongate body; extending the positionable tissue approximating structure from the device; and using the positionable tissue approximating structure to hold severed tissue during anastomosis.

BRIEF DESCRIPTION OF THE DRAWINGS

FIGS. 4, 4a, and 4b schematically illustrate embodiments of an anastomosis devices and methods according to the invention.

FIGS. 6 and 6a schematically illustrate an embodiment of an anastomosis device according to the invention.

FIGS. 7 and 7a schematically illustrates an embodiment of an anastomosis device according to the invention.

FIGS. 9b and 9c are close-up schematic illustrations of portions of FIGS. 9 and 9a, respectively.

FIGS. 10, 10a, 10b, and 10c illustrate one example of a tine support according to the invention. FIG. 10 is a perspective view; FIG. 10a is an end view, FIG. 10b is a side view, and FIG. 10c is a cut-away side view.

All drawings are illustrative, and are not to scale.

DETAILED DESCRIPTION

An anastomosis device according to the invention can be any anastomosis device as described herein to include positionable tissue approximating structure, that can be useful to perform an anastomosis procedure. Much of the following description relates to embodiments of anastomosis devices that include features of a catheter. It will be apparent that features of the inventive devices and methods, while applicable to catheter devices, can also be applied to other anastomosis devices. Similarly, while the following description presents exemplary devices and methods in the context of urethral anastomosis, including radical prostatectomy, it will be apparent that the invention can be applied to other anastomosis procedures that benefit from positionable tissue approximating structure, including but not necessarily only procedures where drainage of fluid is also desired, such as drainage of urine.

Anastomosis devices according to the invention include a flexible elongate body and tissue approximating structure. The tissue approximating structure includes positionable tissue approximating structure and optionally fixed tissue approximating structure. Certain embodiments of devices can also optionally include other related appurtenances including those described herein, such as internal guide structure, lumens, positioning mechanisms, actuating mechanisms, a second flexible elongate body, etc., as desired.

A flexible, elongate body useful for an anastomosis device of the invention can include a proximal end and a distal end, and positionable tissue approximating structure that is positionable relative to the length of the elongate body. The positionable tissue approximating structure may be internal to the elongate body, such as in embodiments that include tines and a tine support that are positionable within the internal hollow space of the elongate body. In alternate embodiments, the positionable tissue approximating structure may be external to the elongate body, such as in embodiments that include a second, outer elongate body that can slide along a length of the first (inner) elongate body of the device, and wherein the second moveable outer elongate body includes tissue approximating structure that moves with the outer elongate body along a length of the inner elongate body.

Figure 6:
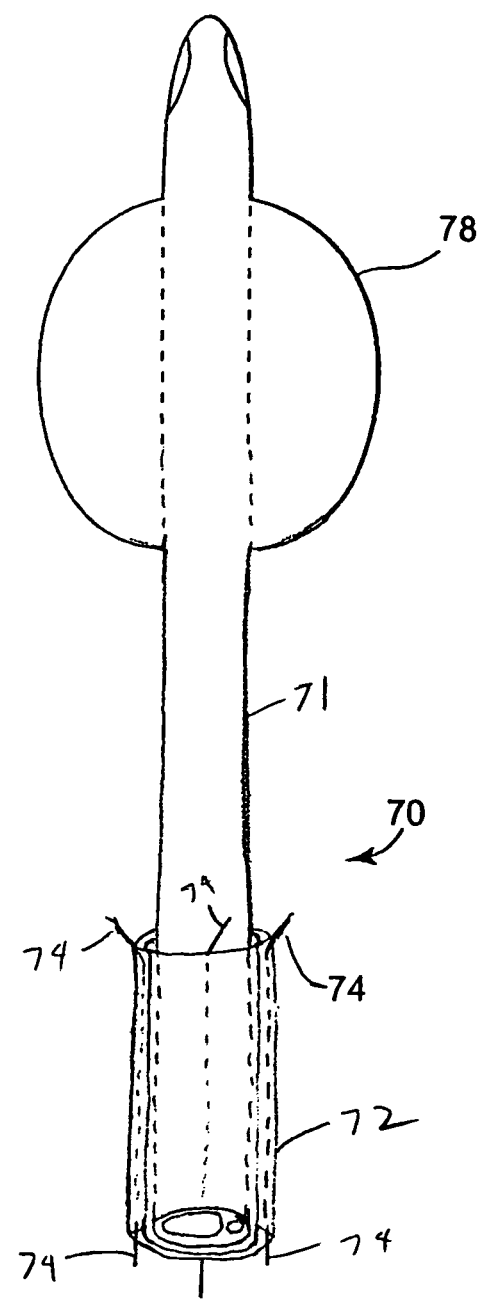
Figure 7:
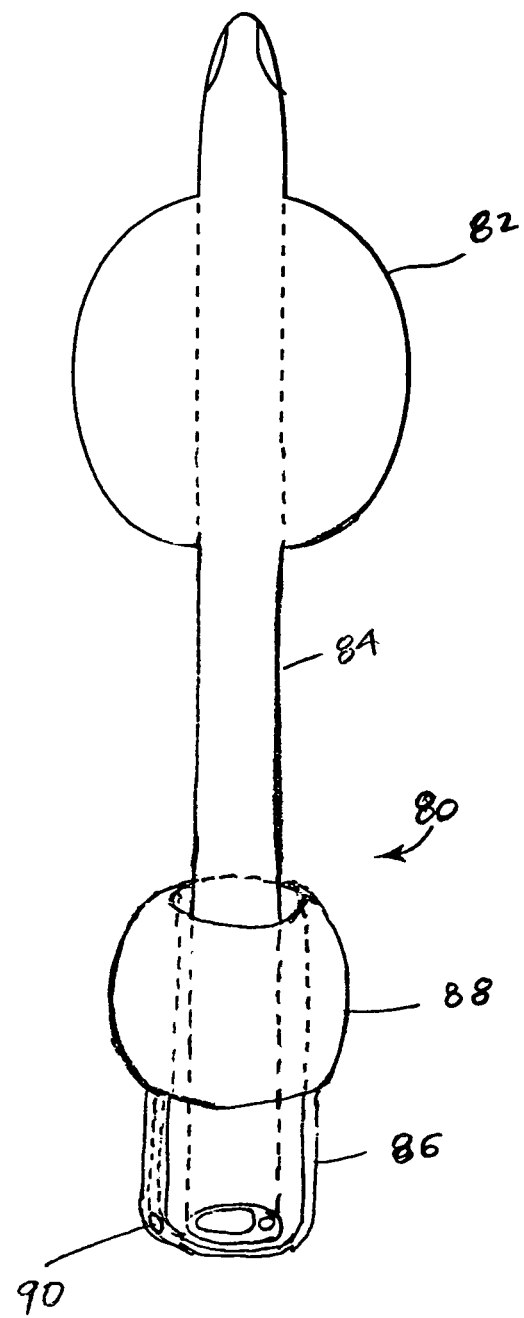

Embodiments of devices of the invention that include an inner elongate body and an outer elongate body (e.g., as illustrated in FIGS. 6 and 7) can allow the advantage of placing tissue approximating structure at a location that is other than the hollow channel within the inner elongate body, which can advantageously eliminate that structure from the space within the inner elongate body. In some certain anastomosis methods, fewer structures being contained in a hollow interior of the elongate body may be advantageous, to reduce the potential for clogging of the inner channel of the elongate body, e.g., by blood clots.

In general, tissue approximating structure (whether positionable or fixed) can include structure that can be incorporated into a anastomosis device, positioned at a desired length and location, either within the interior of the elongate body or outside of the elongate body, and can be any structure useful to hold or otherwise manipulate tissue for healing. An anastomosis device according to the invention can have one or multiple tissue approximating structures, optionally multiple tissue approximating structures that are or can be positioned at different distances along the length of the elongate body to allow the tissue approximating structure to contact and place pressure on opposing severed tissue surfaces when the anastomosis device is installed during an anastomosis procedure and preferably afterward, for healing.

One specific example of structure that can be used as a fixed or positionable tissue approximating structure is a balloon or balloon-like structure. For urethral anastomosis procedures, a balloon may be placed, e.g., inside of a bladder or within the urethra and underneath a perineal floor, to bring severed bladder neck tissue into contact with the severed tissue surface of a urethral stump.

Another type of fixed or positionable tissue approximating structure may include one or multiple elongate structures such as a needle, tine, prod, probe, or the like, which may be positionable or fixed relative to the elongate body, which may have a blunt or a sharp end, and which may be extended from an elongate body of an anastomosis device at a location where the structure can function as a tissue approximating structure. Combinations of balloons and elongate structures may be useful in certain devices and methods of the invention.

Tissue approximating structure, for devices of the invention, does not require and can preferably exclude sutures and any component or structure designed to function in combination with a suture or suturing device such as a needle.

According to the invention, an anastomosis device includes positionable tissue approximating structure that is moveable relative to the elongate body, and optionally can include fixed tissue approximating structure that is fixed in position relative to the elongate body. Thus, various anastomosis devices of the invention can include tissue approximating structure that is positionable, along with a tissue approximating structure that is fixed; two tissue approximating structures that are both positionable; or other combinations of positionable and fixed tissue approximating structures, at least one of which is positionable. Additionally, certain examples of anastomosis devices of the invention can include proximal tissue approximating structure and distal tissue approximating structure, either or both of which may be positionable.

Fixed tissue approximating structure is not moveable (i.e., positionable) relative to the elongate body of an anastomosis device, but is fixed at a location that is desired for a particular anastomosis procedure. When an anastomosis device is installed during an anastomosis procedure, fixed tissue approximating structure is located at a position that allows the tissue approximating structure to be actuated to contact tissue for healing.

An example of fixed tissue approximating structure is a balloon at a distal end (tip) of an anastomosis device. A fixed balloon can be placed into position, during use, to cause contact of two opposing severed tissue surfaces, for example, by being located inside of a bladder wall. With a balloon inside of the bladder, pressure (traction) may optionally be placed on the anastomosis device to pressure the bladder tissue toward another severed tissue, to allow for healing.

Another example of an embodiment of fixed tissue approximating structure can be a sharp, elongate, straight or curved, fine, rigid, structure (i.e., referred to collectively herein as "tines") that can be actuated to extend and retract, e.g., through fixed apertures of an elongate body of an anastomosis device. The elongate structure may be of any rigid material such as plastic, metal, etc., and can be located to extend from the elongate body of the anastomosis device at any useful location along the length of the elongate body. A more specific example of such fixed tissue approximating structure may be an elongate metal tine or other needle-like structure that can be actuated to move from a retracted position inside of the elongate body of the anastomosis device, to an extended position through a pre-formed aperture in the elongate body, by use of an actuating mechanism that extends to the proximal end of the device. An exemplary anastomosis device may include multiple such elongate structures as part of a single assembly that can be extended in different directions (radially) from a desired position (lengthwise) along the elongate body. Optionally, guides such as a metal, ceramic, rigid plastic, or polymeric guides can reinforce pre-formed apertures in the wall of the elongate body through which the multiple elongate structures can be extended and retracted.

Positionable tissue approximating structure is tissue approximating structure that can be moved (i.e., positioned) along at least a portion of the length of an elongate body of an anastomosis device, to a location that is desired for a particular anastomosis procedure. For instance, a positionable tissue approximating structure can be moved to a location along the length of the elongate body that corresponds to the position of body tissue that has been cut or severed, or tissue that is nearby such tissue. Once in a desired position, the positionable tissue approximating structure can be extended from the elongate body of the anastomosis device to contact tissue and move or hold tissue in position. The tissue approximating structure can facilitate movement of tissue by movement of the anastomosis device or a portion of the anastomosis device (e.g., the tissue approximation structure), if desired, and can hold the tissue in place for healing. A positionable tissue approximating structure can be located within a hollow internal space of the hollow elongate body (e.g., such as tines as described herein), or outside of the elongate body (e.g., such as tissue approximating structure located in a hollow outer body as described herein).

One more specific example of positionable tissue approximating structure can be structure of a type that includes an elongate structure (e.g., a sharp-ended tine, or similar structure, referred to collectively herein as a "tine") that can be positioned within the internal hollow portion of an elongate body, then actuated to extend from the elongate body to contact a desired tissue. Once extended to contact tissue, certain embodiments of such tines may optionally be positioned or re-positioned after being extended, to position or re-position contacted tissue.

In certain embodiments, a tine may be sufficiently pointed or sharp to penetrate through the wall of the elongate body when actuated. Alternately, a positionable tine may extend through a pre-formed aperture or length-wise slot in the elongate body. A pre-formed length-wise slot can have the advantage of allowing movement of the tine within the length of the slot after the tine has been extended from the body.

For positionable tissue approximating structure in the form of tines, the number of tines can be any useful number, such as 1, 2, 3, 4, or 6 or more tines in a tine assembly, e.g., to extend in different directions radially from a longitudinal axis of an elongate body. Multiple tines, e.g., 3, 4, or 6, can be collected and bound or secured together into a single assembly of tines ("tine assembly") that can be positioned and actuated together, e.g., by a single positioning mechanism and a single actuating mechanism. More specifically, embodiments of positionable tine assemblies can be connected to a tine positioning mechanism and a tine actuating mechanism, such as rigid or semi-rigid metal wires that can both extend from the tine assembly, along a length of the anastomosis device, to a proximal end of an anastomosis device for manipulation.

Another feature of certain types of positionable tissue approximating structure, e.g., those that include positionable tines as tissue approximating structure, can be a tine support structure ("tine support"), which is a structure that can position and support one or multiple tines either within the elongate body or outside of the elongate body, e.g., to allow the tines to be positioned along a length of the elongate body and actuated. A tine support can be any structure that provides support for a tine, allows positioning of a tine, or guides a tine during actuation. In general, such a support structure will include apertures, channels, or holes, through which one tine will pass during use and actuation (e.g., extension and retraction) and will be connected to the proximal end of a device by a positioning mechanism, which may be a wire, tube or hollow body, etc.

One example of a tine support can be a solid body that fits within the hollow interior of an elongate body of an anastomosis device and that can be moved along a length of the elongate body. The solid body of such a tine support can include one or multiple pre-formed apertures and internal channels, e.g., one channel to guide and support each of one or more tines. Various non-limiting examples of this type of tine support are illustrated in FIGS. 10, 10a, 10b, 10c, 11, 12, 13, and others of the attached figures.

Referring specifically to tine supports that are internal to an elongate body of an anastomosis device, the shape and form of a such a tine support can be any shape and form that can be useful to allow an elongate structure such as a tine to be positioned, and then actuated, as part of an anastomosis device as described herein. Certain embodiments of tine supports can be of a shape and size that fits within a hollow interior of an elongate body of an anastomosis device, to allow movement and positioning of the positionable tissue approximating structure (tine support and tines) along a length of the elongate body. The tine support can be designed to work with multiple tines, either as a single set of tines (e.g., either a proximal or distal tine assembly) or multiple sets of tines (e.g., both a proximal tine assembly and a distal tine assembly).

Structure such as apertures and channels can be included as guides within a body of a tine support, for various purposes, including to support and preferably guide or deflect tines during actuation, or to allow passage of mechanisms through the tine support. For example, a tine support may include apertures and channels that enter at an end of a body of a support and exit at a side of the support. Such a channel can guide and deflect a tine from a position generally along the axis of the elongate body, to a direction that extends from the elongate body, during actuation. A tine support may also include apertures and channels that extend from end-to-end through a body of a tine support, e.g., along or parallel to a longitudinal axis of the body, e.g., at or near the center of the body. Such a channel can be used to allow passage of a positioning mechanism or an actuating mechanism associated with one or more tissue approximating structures.

The outer surface of a tine support can be of any useful or desired shape, size, and form, e.g., round, angled, channeled, etc., and can have a diameter that allows movement of the tine support within an elongate body of an anastomosis device, e.g., including a diameter that is less than the interior diameter of an elongate body. A tine support may optionally include a shape or structure that engages an adjacent or opposing structure of an interior surface of an elongate body, e.g., that extends along a length of an internal surface of an elongate body, the interrelated structures being useful to inhibit or prevent rotational movement of the tine support (i.e., movement around a longitudinal axis of the tine support) within the elongate body during use. Such structure (e.g., "guide" structure) of a tine support can be in the form of a specific curved or angled cross-sectional shape of a tine support body such a triangle, square, hexagon, etc; an extension of the body; a recess of the body such as one or multiple recessed channels; one or multiple extended ribs, peaks, plateaus, or other surface extensions; etc.; of the tine support body, that engage an opposing or corresponding structure at the internal surface of an elongate body. A guide structure may extend along a length of a body of a tine support, or may be located at one end, at both ends, or at a central location along a length of a tine support. Multiple, symmetrical guide structures may be useful, or just one or two structures, as will be appreciated.

Another example of a structure that can perform as a tine support can be a second (outer) hollow body that fits around and is moveable relative to the (first) elongate body of the anastomosis device, wherein the second hollow body has fixed apertures or channels in the wall through which tines can be extended. Non-limiting examples of this type of tine support, wherein the support is in the form of an outer body that is positionable relative to the first elongate body of an anastomosis device, are illustrated in FIGS. 6 and 6a.

Thus, examples of tissue approximating structure located outside of the elongate body is a type of tissue approximating structure that includes a second (outer) hollow elongate body that extends along a portion of the ("first" or "inner") hollow elongate body and that is moveable along the "first" hollow elongate body. For example, an outer hollow body can be fit to move length-wise outside of the inner hollow body, and may include a tissue approximating structure in the form of tines or a balloon. If tissue approximating structure includes tines, the tines and an actuating mechanism can extend within the wall of the outer body such that the actuating mechanism extends to the proximal end of the outer body, to extend and retract the tines from the outer body. If tissue approximating structure includes a balloon, an inflation lumen may extend within the wall of the outer body such that the lumen extends to the proximal end of the outer body to allow for inflation of the balloon.

An anastomosis device may include multiple tine supports, such as a tine support associated with positionable, proximal tissue approximating structure; a tine support associated with positionable, distal tissue approximating structure; or both. Thus, embodiments of the invention can include an anastomosis device that includes two separate positionable tine supports, one each for a positionable distal tissue approximating structure and a positionable proximal tissue approximating structure, wherein each positionable tissue approximating structure is positionable relative to the elongate body and relative to the other positionable tissue approximating structure. As an alternative, an anastomosis device may include just one positionable tine support that is used with both proximal and distal tissue approximating structure, both of which are positionable relative to the elongate body, but which are fixed in position relative to each other.

A tine support may include or be connected to a positioning mechanism that allows the tine support to be moved along a length of the elongate body. A positioning mechanism can be any structure that allows such positioning, e.g., a flexible metal wire or a hollow (e.g., polymeric) tube or elongate body that is part of or that is secured to a tine support, e.g., that can extend from the tine support to the proximal end of an anastomosis device. A positioning mechanism may be internal to or external to the hollow body. Desirably, a positioning mechanism can be manipulated, at a proximal end of an anastomosis device, to move the positionable tissue approximating structure to a desired position along a length of the hollow elongate body. According to such an overall combination of structures, embodiments of positionable tissue approximating structure can be moved along a length of the elongate body by manipulating the positioning mechanism at the proximal end of the anastomosis device.

In other embodiments, a positioning mechanism may be in the form of an outer elongate body. For instance, positionable tissue approximating structure in the form a positionable balloon that is part of an outer elongate body can be positioned by moving the outer elongate body. According these and similar embodiments, the outer body can be considered to be a positioning mechanism.

Once a desired position for a tissue approximating structure is achieved, a positioning mechanism can be fixed to maintain the position of the positionable tissue approximating structure, and the positionable tissue approximating structure can be extended (and optionally retracted) away from the body of the anastomosis device. In the specific embodiment of a tine assembly within the interior space of a hollow elongate body, tissue approximating structure in the form of one or multiple tines can be extended through the wall of the elongate body (e.g., by penetrating the wall or be extending through an aperture or slot) to contact desired tissue for anastomosis. In the specific embodiment of a tine or tines that are included in a second hollow (exterior) elongate body that moves along the outside of the (first) hollow elongate body, such tines can be extended through fixed channels or apertures of the exterior elongate body to contact desired tissue. In the specific embodiment of a balloon included as tissue approximating structure in a second hollow (exterior) elongate body that moves along the outside of the (first) elongate body, the balloon can be inflated (i.e., extended from the anastomosis device) by use of an inflation lumen that connects the balloon to the proximal end of the outer elongate body, e.g., that reaches the proximal end of the anastomosis device.

As is apparent from the present description of exemplary tissue approximating structures, various embodiments of devices of the invention can include a positionable tissue approximating structure that is capable of being positioned either prior to or after actuating the tissue approximating structure to contact desired tissue. As an example, tissue approximating structure that includes tines internal to an elongate body, that can be actuated to extended (or retracted) from the elongate body, may be moved into position prior to being actuated. Such internally-located tines may or may not be moved after being actuated. Specifically, embodiments of devices that allow movement of positionable tissue approximating structure after the structure is actuated, may include an elongate body that includes apertures, e.g., length-wise slots along a portion of the length of the elongate body through which the tines or other elongate approximating structure are extended. The elongate approximating structure can move along the length of the slots even after being actuated, to allow for movement of the elongate approximating structure after contact with tissue, e.g., to adjust or allow movement of the tissue.

Another embodiment of a device that allows movement of positionable tissue approximating structure after the structure is actuated may include an anastomosis device that includes an outer elongate body around an inner elongate body, wherein the outer body can be moved along the length of the inner body, and the outer body includes tissue approximating structure. The tissue approximating structure of the outer body can be actuated (e.g., times may be extended or a balloon may be inflated), and the outer body may then slide length-wise over the inner body, while the tissue approximating structure is actuated. The ability to move the outer body after the tissue approximating structure has been actuated allows for movement of the approximating structure after it has come into contact with tissue, e.g., to adjust or allow movement of the tissue.

Certain embodiments of anastomosis devices according to the invention can contain various lumens, e.g., for inflating a balloon, for drainage, for containing a positioning mechanism or an actuating mechanism, for tissue approximating structure, etc., as well as positioning and actuating mechanisms, running along a length of an elongate body. Lumens can be arranged in any useful configuration such as coaxially, side-by-side, internal to a wall of an elongate body, or according to any other useful configuration. A lumen or a mechanism (e.g., a positioning mechanism or an actuating mechanism) that runs along a length of the elongate body may be diverted at the proximal end of the catheter body to a port that provides access to the lumen or mechanism during use, as is known.

A central lumen can be a central hollow elongate space running along a length of an elongate body. A central lumen can contain one or more positionable tissue approximating structures or components thereof, including, e.g., a tine support, tines, a tine assembly, a positioning mechanism, an actuating mechanism, etc. A central lumen can also be used for fluid flow such as drainage, e.g., to drain urine from a bladder. An example of another lumen can be an inflation lumen that can extend from a proximal end of a device to a balloon, e.g., within a wall of an elongate body.

Specific examples of devices and components of devices of the invention are described below with reference to figures of exemplary such devices and components.

One exemplary embodiment of a tine support is illustrated at FIGS. 10, 10a, 10b, and 10c. Referring to the perspective view of FIG. 10, tine support 130 includes body 136 having multiple apertures 132 and 134 connected by an internal channel (not shown) through body 136. Apertures 132 receive a tine, and the tine enters the internal channel defined within body 136, through which a tine can be deflected to exit aperture 134. Aperture 144 is also shown at the distal end of the support body 136. Aperture 144 is at the end of a central channel (not shown) extending longitudinally through the length of body 136. The central channel can receive at a proximal end of the body 136, through an aperture (not shown), an actuating mechanism that passes through the central channel and exits aperture 144 at the distal end. A total of 12 deflecting channels are internal to body 136, six spaced around the circumference toward each of the two ends of body 136. Tine support 130 includes two ends, proximal end 138 and distal end 140, each of which includes channels to guide six tines. Thus, this embodiment of a tine support can be used to position and actuate two sets each of six tines, for example one assembly of six tines that makes up a distal tine assembly (not shown) and one assembly of six tines that makes up a proximal tine assembly (not shown). Proximal end 138 includes extension 147 adapted to connect to a positioning mechanism in the form of a hollow elongate tube.

Figure 10A:
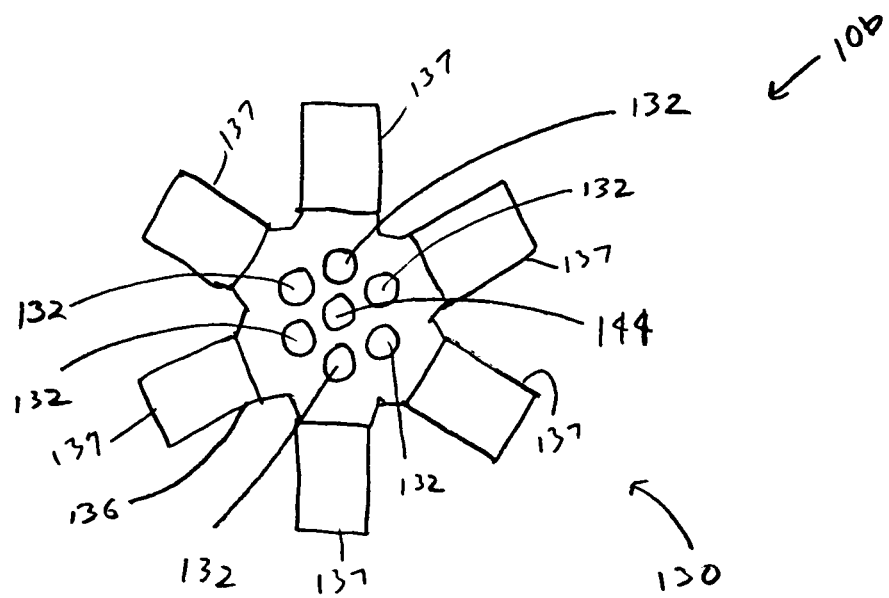

Referring still to FIG. 10, ribs 137 extend from the central portion of body 136, outwardly as guide structures. Ribs 137 also define channels between the ribs, which can correspond to opposing structure at an interior surface of a wall of a hollow elongate body of an anastomosis device (see, e.g., FIG. 11). Ribs 137 and channels of the tine structure 130, along with corresponding structure of in internal surface of an elongate body, can inhibit rotational movement of this embodiment of a tine support within a hollow elongate body. While FIG. 10a shows a body 136 having 6 ribs 137, any number of ribs, e.g., from 1 to 6, such as 2, 3, 4, etc., could be useful.

Figure 11:
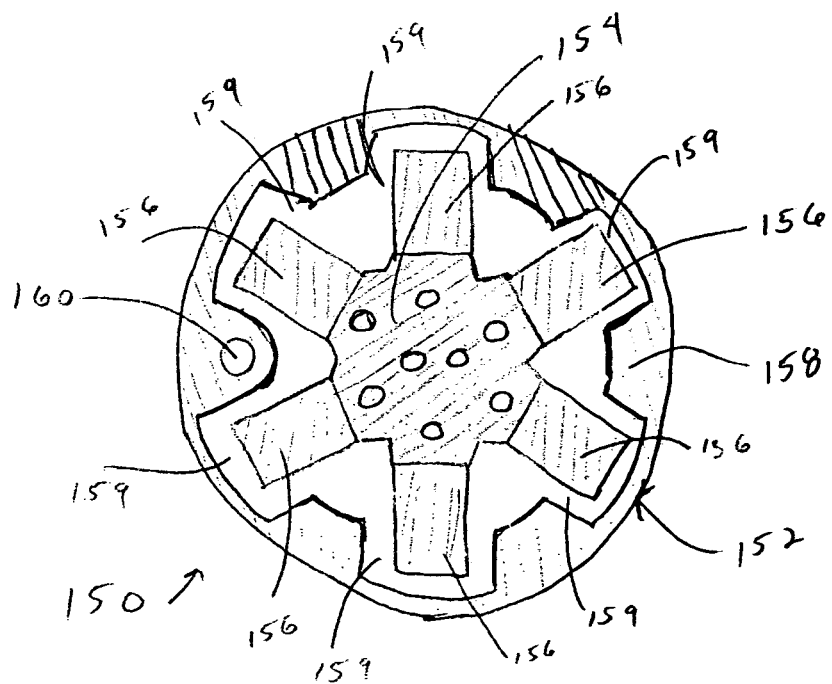
FIG. 11 illustrates an end view of a cross section of an embodiment of an anastomosis device of the invention, including a hollow elongate body containing a tine support.

FIG. 11 shows an example, in cross-section, of an anastomosis device according to the invention that includes guide structure to inhibit rotational movement of a tine support within an elongate body. Referring to FIG. 11, anastomosis device 150 includes hollow elongate body 152 and tine support 154, each shown in cross section. Tine support 154 can be a proximal tine support, a distal tine support, or may be a single tine support that supports both distal and proximal tine assemblies. Tine support 154 includes ribs 156 that extend into channels 159 defined by and between ribs 158 of the interior surface of hollow elongate body 152. The example in FIG. 11 of a cross-section of an anastomosis device shows 6 ribs and 6 channels, with a symmetrical cross section. Alternatively, more or fewer ribs could be included and a symmetrical cross-section is not required. Lumen 160 is illustrated to be within one of the ribs 158 of elongate body 152. Such a lumen, or multiple lumens, can be used for understood purposes, such as an inflation lumen that connects a balloon at a distal end of the anastomosis device to a proximal end of the same device. The combination of opposing ribs 156 and channels 159 can also be sized to include free space within the central channel of the elongate body for drainage, e.g., for urine drainage in a urethral catheter embodiment of the invention. Also, while FIG. 11 shows a body 152 having 6 ribs 156, and six corresponding channels 159, any number of ribs and channels, e.g., from 1 to 6, such as 2, 3, 4, etc., could be useful.

Referring now to FIG. 10a, illustrating an end view of tine support 130, 6 apertures 132 are shown. Each aperture 132 can receive a tine, and each aperture 132 is in communication with an arcuate channel (not shown) that extends internally within body 136, which channels can guide and deflect a tine such that the tine can be extended and retracted from tine support 130 by an actuating mechanism. Ribs 137 are shown. Also shown is central aperture 144, which extends through the entire tine support 130 from end to end. Central aperture 144 can be used, for example, to allow passage of a positioning mechanism used to position a different (e.g., distant) tine support of the same anastomosis device, or may be used to allow passage of an actuating mechanism that can be used to actuate tines of tine support 130 or tines of a different tine support of the same anastomosis device. Additional central apertures can also be included, even though not shown, to allow passage of additional positioning or actuating mechanisms.

FIG. 10*b* shows a side view of an example of tine support 130. Tine support 130 is shown to include apertures 134, ribs 137, distal end 140, and proximal end 138. (Apertures 132 are not shown.) Proximal end 138 includes land area 146 and extension 147. Land area 146 and extension 147 are designed and size to receive a positioning mechanism in the form of a hollow tube (not shown), which extends over extension 147 and seats against land area 146. The hollow tube positioning mechanism can extend through a length of an anastomosis device, from tine support 130 to a proximal end of an anastomosis device, and can be used to move and position tine support 130 along a length of such an anastomosis device.

FIG. 10*c* shows a cross-sectional side view of tine support 130. FIG. 10*c* shows channels 142 extending between apertures 132 and 134. These channels guide a tine (not shown) through the body of tine support 130 when a tines actuated, directing the tine toward a wall of an elongate body of an anastomosis device, and then through the wall of the anastomosis device, to contact and approximate a body tissue.

In general, a tine support such as tine support 130 of FIG. 10*c*, can cause tines to be actuated to extend from an elongate body, at any angle relative to the axis of the elongate body, e.g., a shallow angle, a perpendicular angle, or even a sharp angle that is greater than ninety degrees from perpendicular to the axis of the elongate body.

Figure 12:
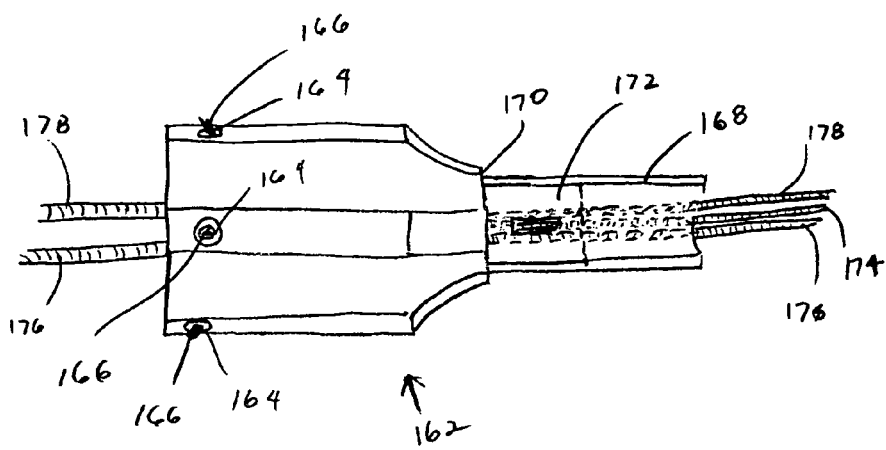
FIG. 12 is a side view illustration of an embodiment of a positionable tissue approximating structure of the invention, including a tine support and tines.

Another example of a positionable tine support is shown in FIG. 12. FIG. 12 shows tine support 162, which is a positionable proximal tine support for use with an anastomosis device that includes separate distal and proximal tine supports, and wherein at least the proximal tine support is positionable. Tine support 162 includes apertures 164 for extension of tines 166. Tine support 162 is positionable along a length of an anastomosis device, and can be moved and positioned by use of positioning mechanism 168 which is a hollow tube that seats against surface 170 and over extension 172 to secure to support 162. Positioning mechanism 168 can extend to a proximal end of an anastomosis device and can be moved to position tine support 162 at a desired position along a length of an elongate body of an anastomosis device. Once positioned, tines 166 can be extended by use of actuating mechanism 174, which is a solid wire that also extends to a proximal end of an anastomosis device. Actuating mechanism 174 can be manipulated to cause tines 166 to extend or retract from body 162, and through a solid wall or an aperture of a hollow elongate body (not shown) of an anastomosis device.

Also shown in FIG. 12 are positioning mechanism 178 and actuating mechanism 176, relating to a distal tine support and distal tine assembly. Positioning mechanism 178, shown as a flexible wire, runs through a channel (not shown) within tine support 162, exiting the distal side of tine support 162 and extending within an elongate body of an anastomosis device (not shown) to a distal tine support (not shown) where positioning mechanism 178 is secured to the distal tine support. Positioning mechanism 178 connects to the distal tine support and extends to a proximal end of an anastomosis device, where the positioning mechanism can be used to move and position the distal tine support along a length of the anastomosis device. Actuating mechanism 176 also runs from a proximal end of an anastomosis device, through tine support 162, and to a tine structure associated with the distal tine support.

Figure 13:
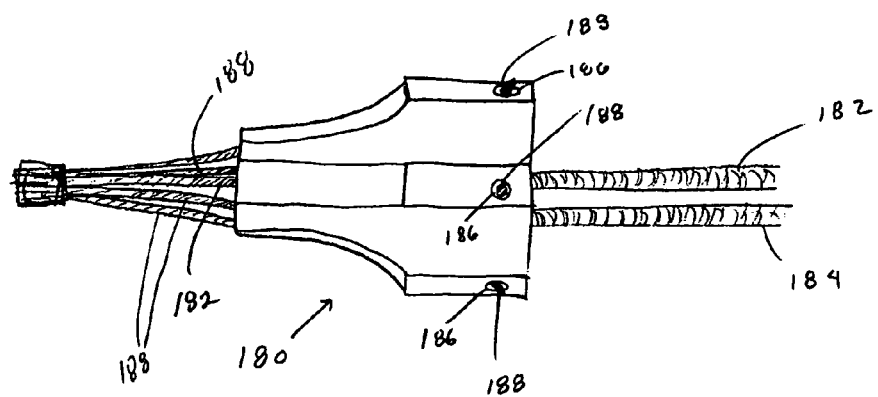
FIG. 13 is a side view illustration of an embodiment of a positionable tissue approximating structure of the invention, including a tine support and tines.

Another example of a positionable tine support is shown in FIG. 13, which shows tine support 180, a positionable, distal tine support for use with an anastomosis device that includes separate distal and proximal tine supports, wherein at least the distal tine support is positionable. Positionable tine support 180 includes apertures 186 for extension of tines 188. Tine support 180 is positionable along a length of an anastomosis device, and can be moved and positioned using positioning mechanism 184, which is shown as a wire that secures to tine support 180. Positioning mechanism 184 can extend to a proximal end of an anastomosis device (optionally but not necessarily through a channel or aperture in a proximal tissue approximating structure) and can be manipulated to position tine support 180 at a desired position along a length of an elongate body of an anastomosis device. Once positioned, tines 188 can be extended (and retracted) by use of actuating mechanism 182, which is a solid wire that also extends to a proximal end of an anastomosis device, (optionally but not necessarily through a channel or aperture in a proximal tissue approximating structure). Actuating mechanism 182 passes through a channel (not shown) in support 180 and connects to tines 188 at the distal side of the support 180. Actuating mechanism 182 can be manipulated to cause tines 188 to extend or retract from support 180, to extend (and be retracted) through a wall of a hollow elongate body (not shown) of an anastomosis device.

Figure 14:
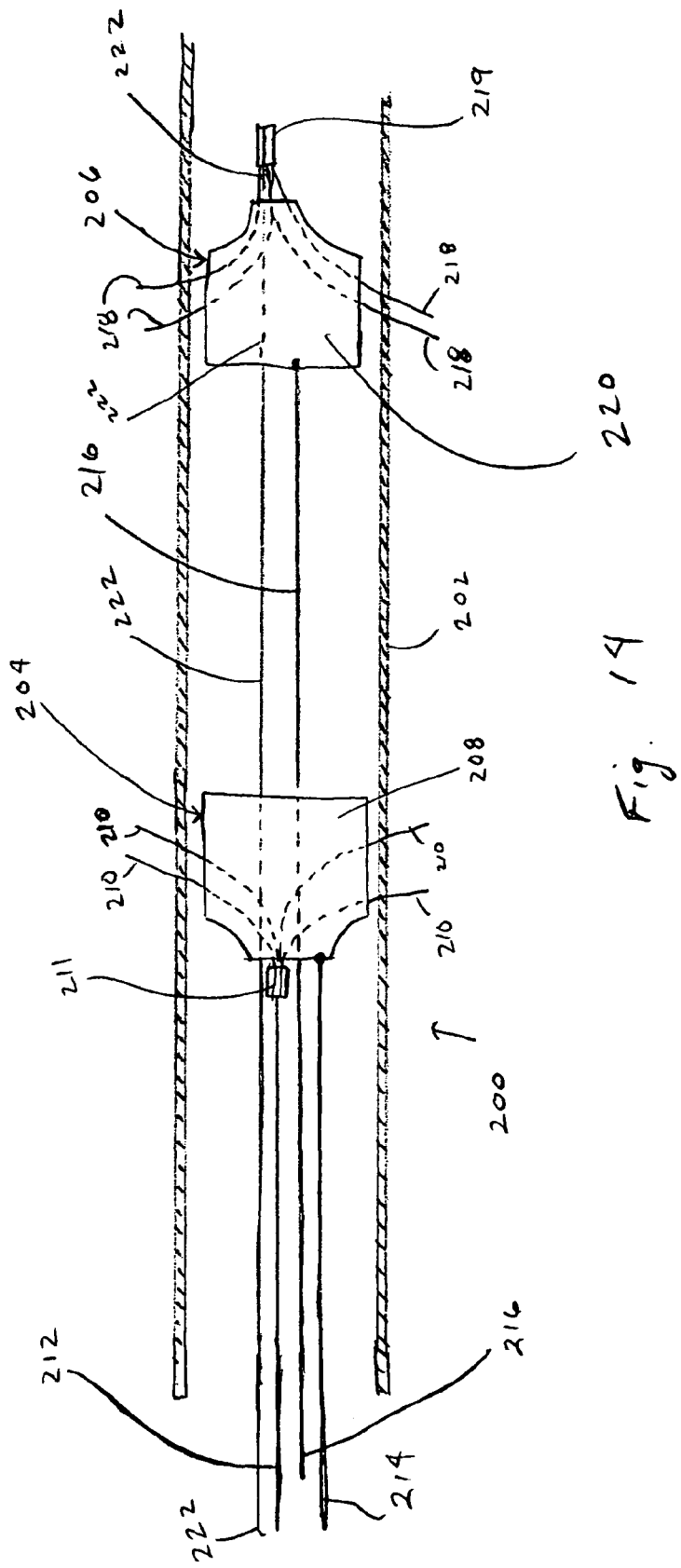
FIG. 14 is a side view cut-away illustration of an embodiment of a device of the invention that includes a hollow elongate body and positionable distal and positionable proximal tissue approximating structures, each including a separate tine support body and tines.

One example of an anastomosis device according to the invention is shown at FIG. 14. FIG. 14 shows a length of anastomosis device 200, which includes elongate body 202, proximal tissue approximating structure 204, and distal tissue approximating structure 206.

Referring still to FIG. 14, proximal tissue approximating structure 204 includes proximal tine support 208 and proximal tines 210. Four proximal tines, 210, are illustrated as part of the proximal tine assembly, bound together by binding mechanism 211. Alternately, a tine assembly may be prepared as a single piece or single unit construction. More or fewer than four proximal tines may be used, e.g., 1, 2, or 6. Proximal tissue approximating structure positioning mechanism 214, shown as a wire, connects to proximal tine support 208 and extends to a proximal end of the anastomosis device (not shown). Positioning mechanism 214 can be used to position proximal tine support 208 at different desired locations along a length of elongate body 202. Once proximal tine support 208 is positioned as desired, proximal tines 210 can be actuated, i.e., extended and optionally retracted, e.g., by fixing positioning mechanism 214 and moving proximal tine actuating mechanism 212. Proximal tines 210, as illustrated, are in an extended orientation, extending from proximal tine support 208 and through the wall of elongate body 202. Optionally, the tines may extend through a slot (not shown) that extends along a length of elongate body 202.

Referring still to FIG. 14, distal tissue approximating structure 206 includes tine support 220 and distal tines 218. Four tines, 218, are illustrated as part of the distal tine assembly, bound together by a binding mechanism 219. More or fewer than four distal tines may be used, e.g., 1, 2, or 6. Distal tissue approximating structure positioning mechanism 216 connects to distal tine support 220 and passes through an aperture (not shown) in proximal tine support 208 to extend to a proximal end (not shown) of the anastomosis device. Distal tissue approximating structure positioning mechanism 216 can be used to position distal tine support 220 along a length of elongate body 202. Once distal tine support 220 is positioned as desired, distal tines 218 can be actuated, i.e., extended and optionally retracted, e.g., by fixing positioning mechanism 216 and manipulating distal tine actuating mechanism 222, which extends through an aperture (not shown) in distal tine support 220, through an aperture (not shown) in proximal tine support 208, and to a proximal end (not shown) of an anastomosis device. Distal tines 218, as illustrated, extend from tine support 220 and through the wall of elongate body 202. Optionally, the tines may extend through a slot (not shown) that extends along a length of elongate body 202.

Figure 15:
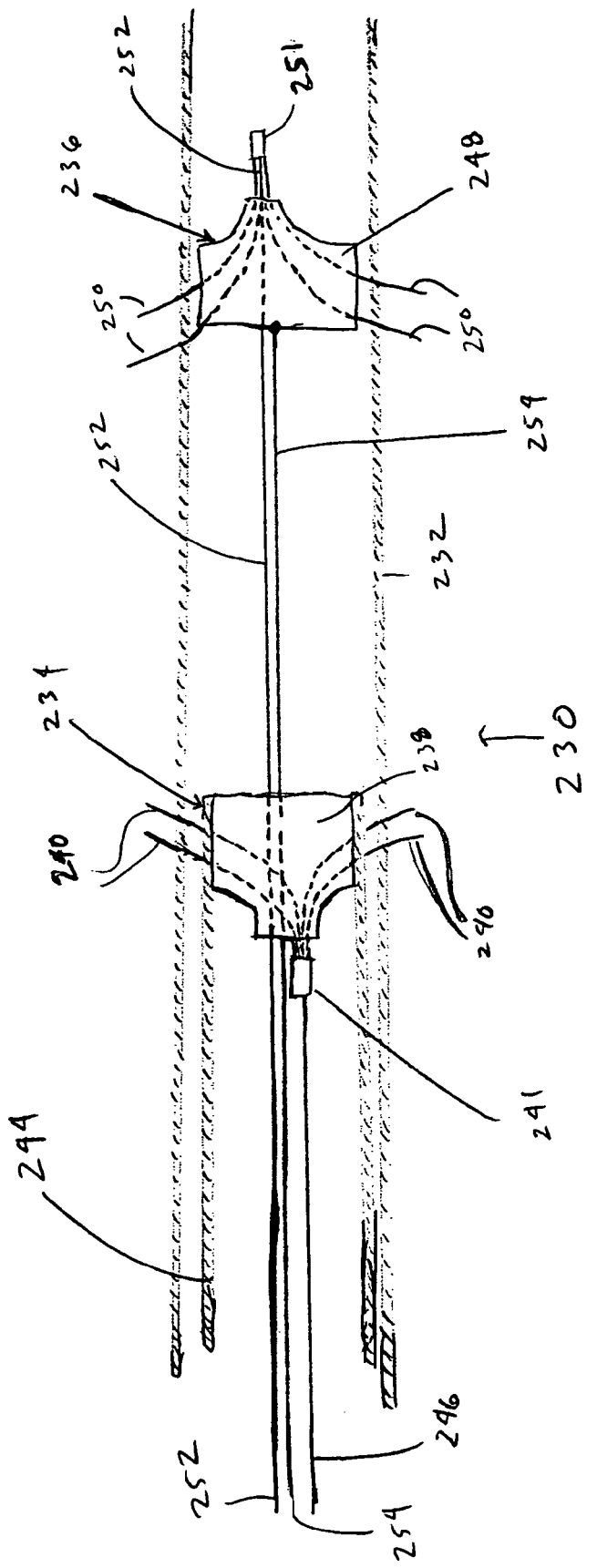
FIG. 15 is a side view cut-away illustration of an embodiment of a device of the invention that includes a hollow elongate body and positionable distal and positionable proximal tissue approximating structures, each including a separate tine support body and tines.

Another example of an anastomosis device according to the invention is shown at FIG. 15. FIG. 15 shows a length of anastomosis device 230, which includes elongate body 232, proximal tissue approximating structure 234, and distal tissue approximating structure 236.

Referring still to FIG. 15, proximal tissue approximating structure 234 includes proximal tine support 238 and proximal tines 240. Four proximal tines, 240, are illustrated as part of a proximal tine assembly, bound together by a binding mechanism 241. Proximal tissue approximating structure positioning mechanism 244 connects to proximal tine support 238, and extends to a proximal end of the anastomosis device (not shown). Positioning mechanism 244 is a hollow tube that bonds to proximal tine support 238, and that contains along its interior, proximal tine actuating mechanism 246 as well as distal tine actuating mechanism 252 and distal tine positioning mechanism 254. Proximal tissue approximating structure positioning mechanism 244 can be used to position proximal tissue approximating structure 234 along a length of elongate body 232. Once proximal tissue approximating structure 234 is positioned as desired, proximal tines 240 can be actuated using proximal tine actuating mechanism 246, e.g., while proximal tine assembly positioning mechanism 244 is secured. Proximal tines 240, as illustrated, are in an extended position, extending from proximal tine support 238 and through the wall of the elongate body 232. Optionally, the tines may extend through a slot (not shown) that extends along a length of elongate body 232.

Referring still to FIG. 15, distal tissue approximating structure 236 includes distal tine support 248 and distal tines 250. Four tines, 250, are illustrated as part of the distal tine assembly, bound together by a binding mechanism 251. More or fewer than four distal tines may be used. Distal tissue approximating structure positioning mechanism 254 connects to distal tine support 248, and extends through an aperture (not shown) in proximal tine support 238, to a proximal end (not shown) of the anastomosis device. Distal positioning mechanism 254 can be used to position distal tine support 248, and distal tines 250, along a length of elongate body 232. Once distal tine structure 248 is positioned as desired, positioning mechanism 254 can be fixed and distal tines 250 can be actuated using distal tine actuating mechanism 252, which also extends through an aperture (not shown) in proximal tine support 238 and then to a proximal end (not shown) of an anastomosis device. Distal tines 250, as illustrated, extend from tine support 248 and through the wall of elongate body 232. Optionally, the tines may extend through a slot (not shown) that extends along a length of elongate body 232.

Figure 16:
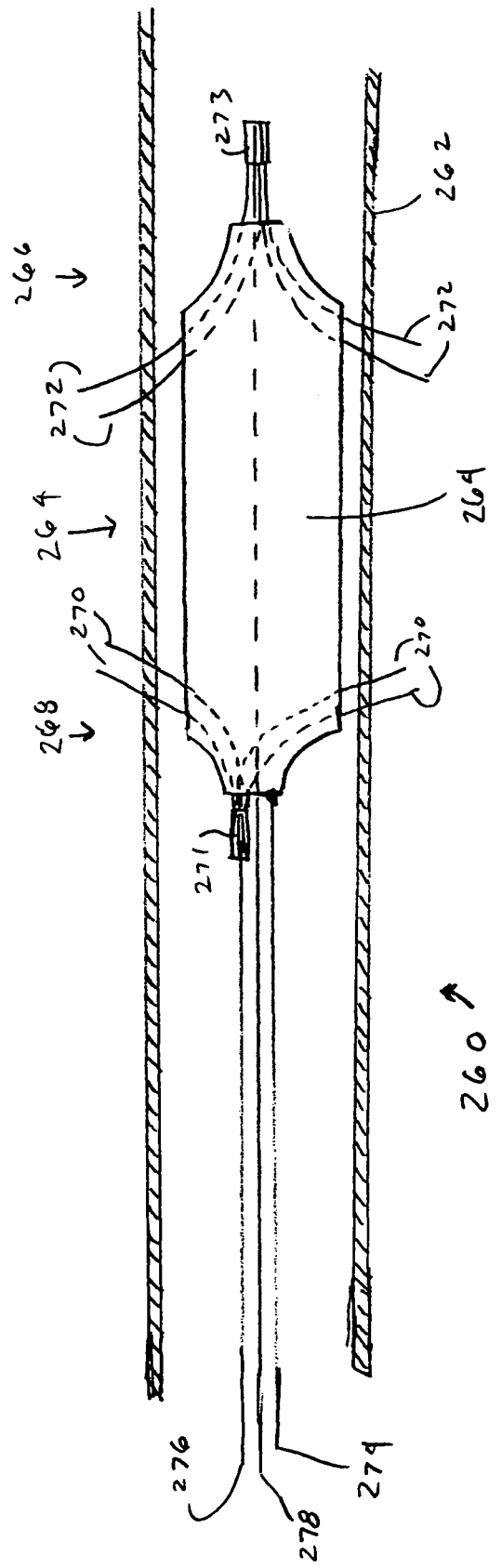
FIG. 16 is a side view cut-away illustration of an embodiment of a device of the invention that includes a hollow elongate body and positionable distal and positionable proximal tissue approximating structures, each structure being part of a single tine support body.

Still another example of an anastomosis device according to the invention is shown at FIG. 16. FIG. 16 shows anastomosis device 260, which includes elongate body 262, proximal tissue approximating structure 268, and distal tissue approximating structure 266. Proximal tissue approximating structure 268 and distal tissue approximating structure 266 share a common positionable tine support, 264, which is used to support proximal tines 270 as well as distal tines 272. Four proximal tines 270 and four distal tines 272 are illustrated, each bound together by binding mechanisms 271 and 273, respectively. More or fewer tines may be included in either or both of the proximal and distal tine assemblies.

Positioning mechanism 274, illustrated as a wire, connects to tine support 264, and extends to a proximal end of the anastomosis device (not shown). Positioning mechanism 274 can be used to position tine support 264, as desired, at a position along a length of elongate body 264. Once proximal tissue approximating structure 264 is positioned as desired, proximal tines 270 can be actuated using proximal tine actuating mechanism 276, e.g., in coordination with control of positioning mechanism 274. Independently of proximal tines 270, distal tines 272 can be actuated using distal tine actuating mechanism 278, which extends through a central aperture (not shown) in tine support 264 and then to a proximal end (not shown) of the anastomosis device.

The exemplary anastomosis devices shown in FIGS. 14, 15, and 16, do not show guide structure that may be present at an internal surface of any of elongate bodies 202, 232, or 262, or at the outer surface of any of tine supports 208, 220, 238, 248, or 264. Even though not illustrated according to these figures, the illustrated inner wall and outer tine support surfaces may optionally included guide surfaces such as described and illustrated elsewhere herein, if desired.

Exemplary embodiments of anastomosis devices according to the invention can include a hollow elongate body and tissue approximating structure, as described, and can additionally include appurtenances such as lumens or other useful features that are sometimes included in catheter devices including those often referred to as Foley catheters. According to such embodiments, an anastomosis device can also operate as a catheter, e.g., for use in vesico-urethral or an end-to-end urethral anastomosis procedures. An anastomosis device that operates as a catheter can include an inflatable balloon located near the distal end, and an inflation lumen extending to the balloon along or within the elongate body. During use, the balloon can rest against the neck of the bladder to prevent urine from entering the neck and to prevent urine from contacting the anastomosis site. Urine at the anastomosis site has the potential to cause difficulties in healing or to cause a stricture, among other deleterious effects. With the balloon blocking the bladder neck during use, urine will pool in the bladder and can be drained from the bladder, for example, using one or more draining apertures at the distal end of the anastomosis device connected to a lumen that connects the draining apertures to a proximal end of the device. A central channel of a hollow elongate body of an anastomosis device may be used as a drainage lumen, or a separate lumen may be included in the device. A drainage lumen can extend from one or more drainage apertures near the distal end, e.g., from apertures near the distal tip, to a location that is at or near the proximal end. As a particular example, a port may be present at the proximal end to connect the drainage lumen to a urine collection device.

Figure 1:
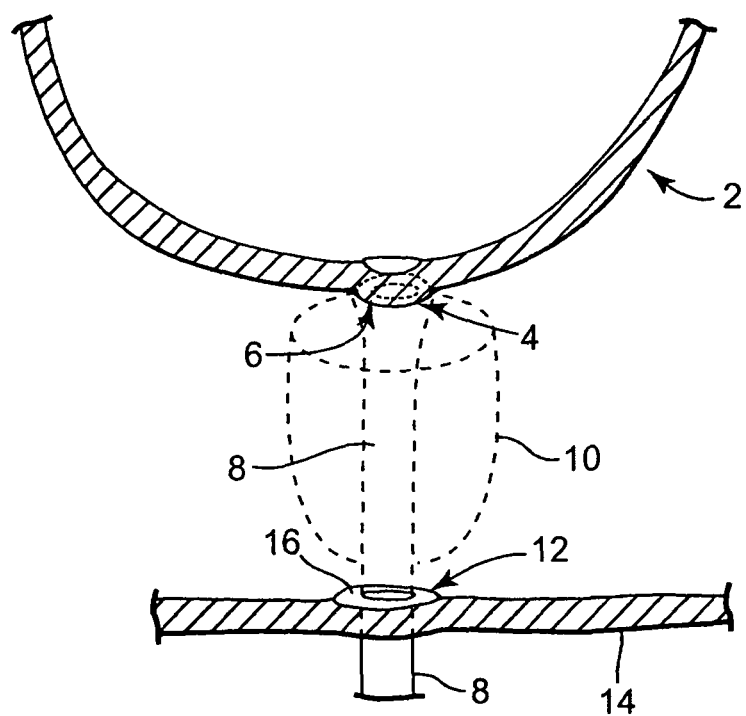
FIG. 1 is a schematic view to illustrate general aspects of radical prostate removal.

One example of an anastomosis procedure according to the invention can incorporate an anastomosis device as described for urethral anastomosis. Referring to FIG. 1, a radical prostatectomy procedure includes removal of the prostate 10 (indicated in dashes) and urethra 8 (also in dashes), leaving bladder 2 with bladder neck 4 having a severed tissue surface 6 at one end of removed urethra 8, and a urethral stump 12 extending from perineal floor 14, with urethral stump 12 having severed tissue surface 16 opposing the severed surface 6 of bladder neck 4.

Figure 9:
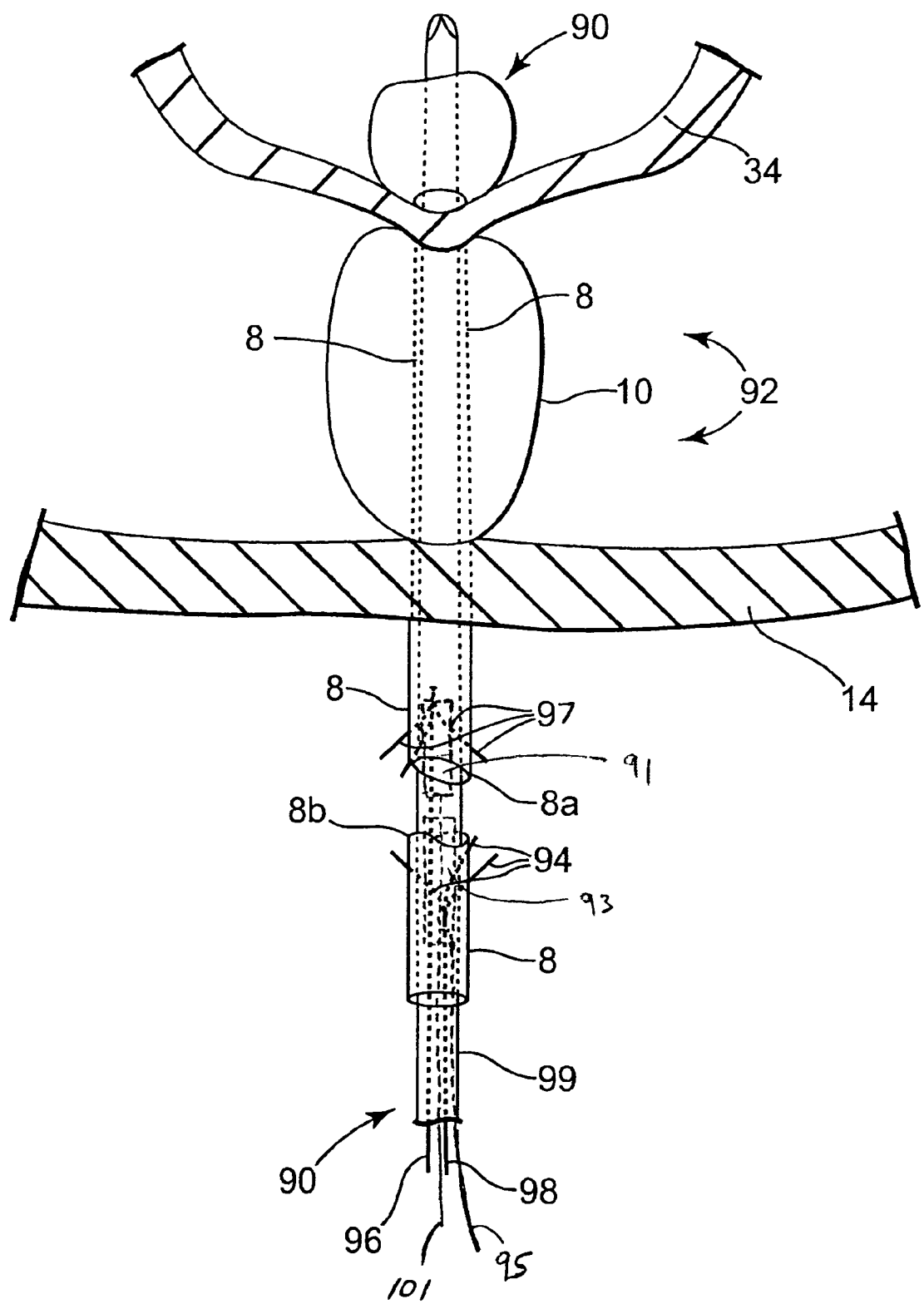
FIGS. 9, 9a, 9b, and 9c schematically illustrate an embodiment of an anastomosis device and a method of the invention.

Another example of a surgical procedure that can include an anastomosis procedure, and which can incorporate a device or method of the present invention, is presented in FIG. 9. Referring to FIG. 9, an end-to-end urethral anastomosis procedure includes a step of severing the urethra 8, below perineal wall 14, to leave two opposing severed urethral tissues 8a and 8b.

Figure 2:
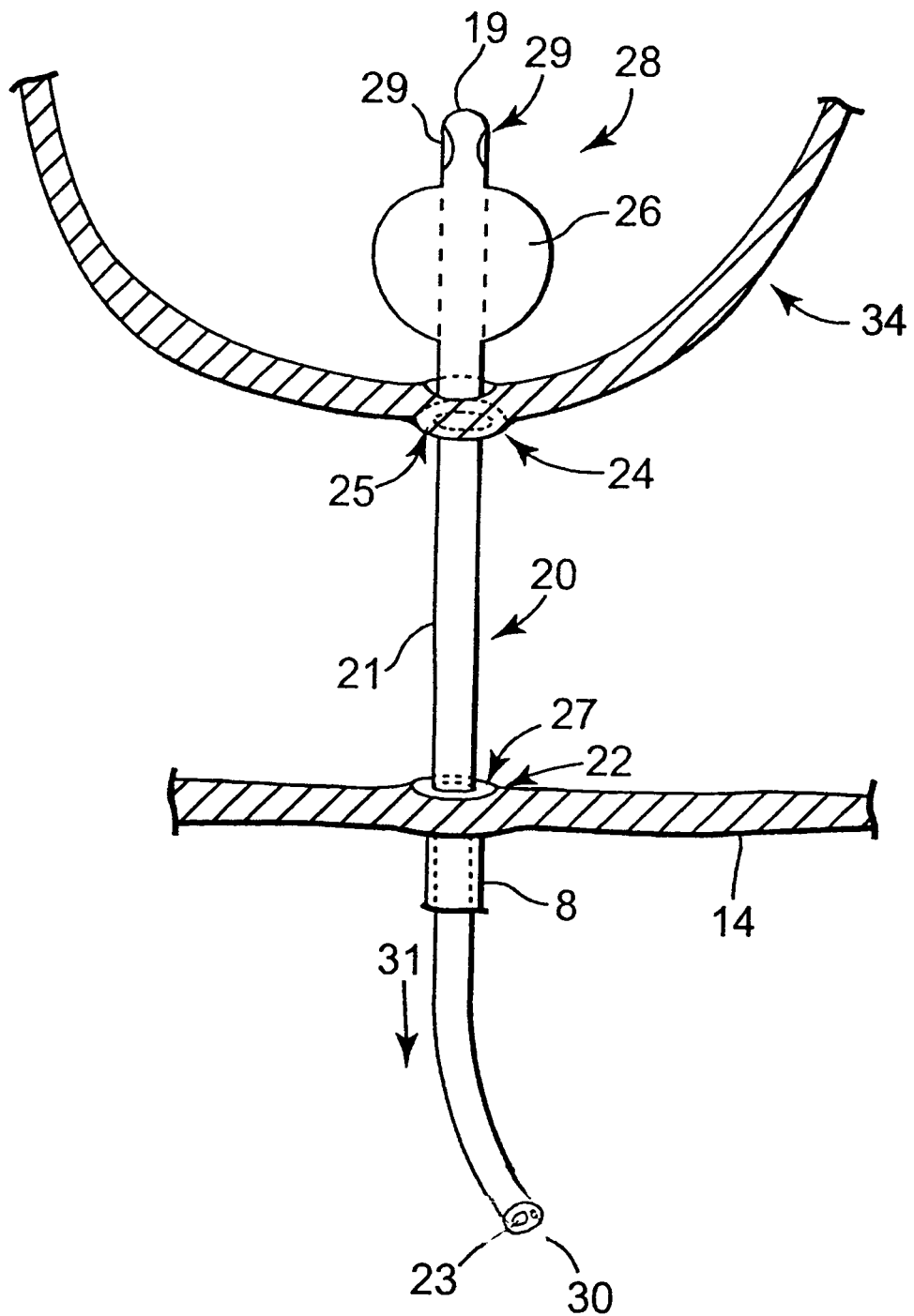
FIGS. 2 and 2a schematically illustrate an embodiment of an anastomosis device according to the invention.
Figure 2A:
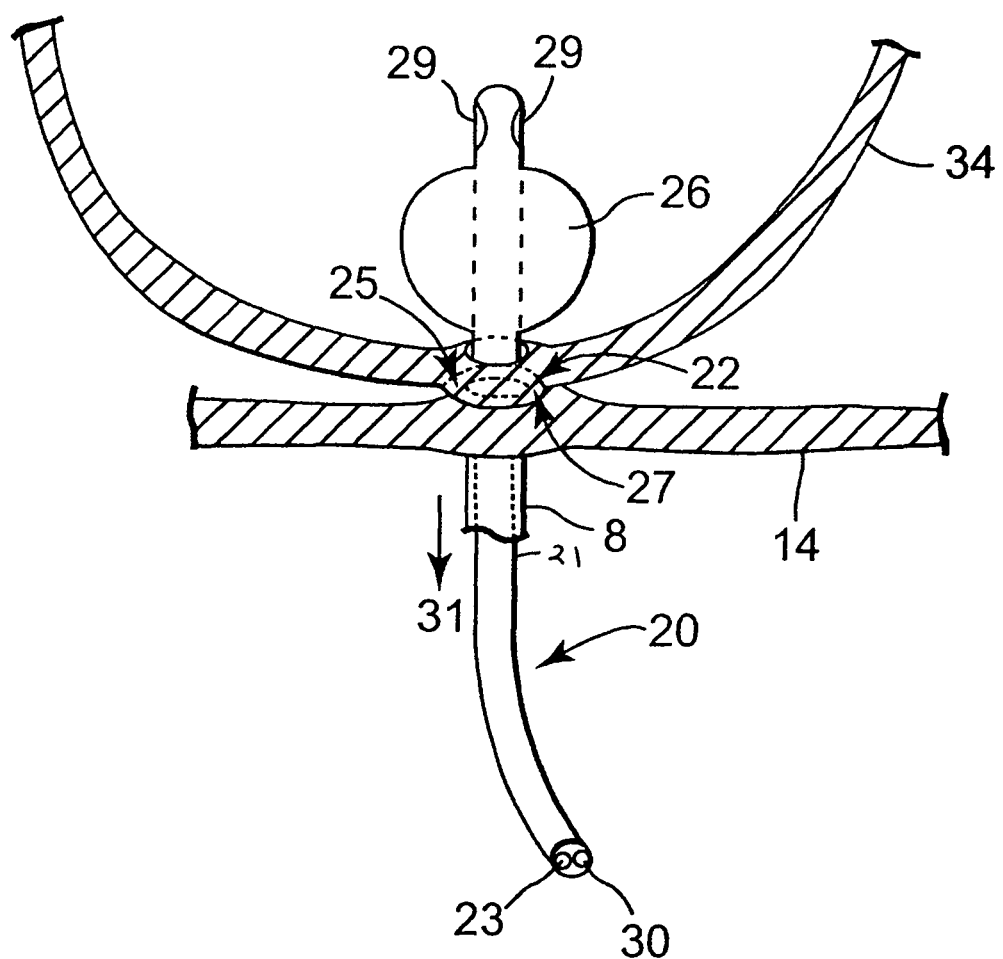

FIGS. 2 and 2a illustrate an embodiment of an anastomosis device of the invention, installed for use within urethra 8 and bladder 34 following removal of a prostate (not shown).

Referring to FIG. 2, a prostate has been removed to leave a severed urethral stump tissue 22 and opposing severed bladder neck 24. Anastomosis device 20 is installed through urethral stump 22 and bladder neck 24. The device 20 comprises an elongate catheter body 21 and balloon 26 located at distal end 28 of device 20. Preferably and as shown, device 20 also includes drain lumen 23 and drain apertures 29 located between the tip 19 of the distal end of the device 20 and balloon 26. Balloon 26 can be inflated, after insertion into bladder 34, by a flow of fluid through balloon lumen 30. Traction (as shown by arrow 31) can then be applied through the length of device 20 to bring the tissues into contact for healing. Details of device 20 such as additional tissue approximating structure are not shown, but can be included in the device as described herein.

Referring to FIG. 2a, balloon 26 can be brought against the interior of the bladder 34 to draw severed bladder neck tissue 25 into contact with severed urethral stump tissue 27. The surface of severed bladder neck tissue 25 can be aligned with the surface 27 of severed urethral stump 22, around and along the axis of the catheter body 21, provided that no gap exists between the surfaces 25 and 27 of the respective severed tissues.

Figure 3:
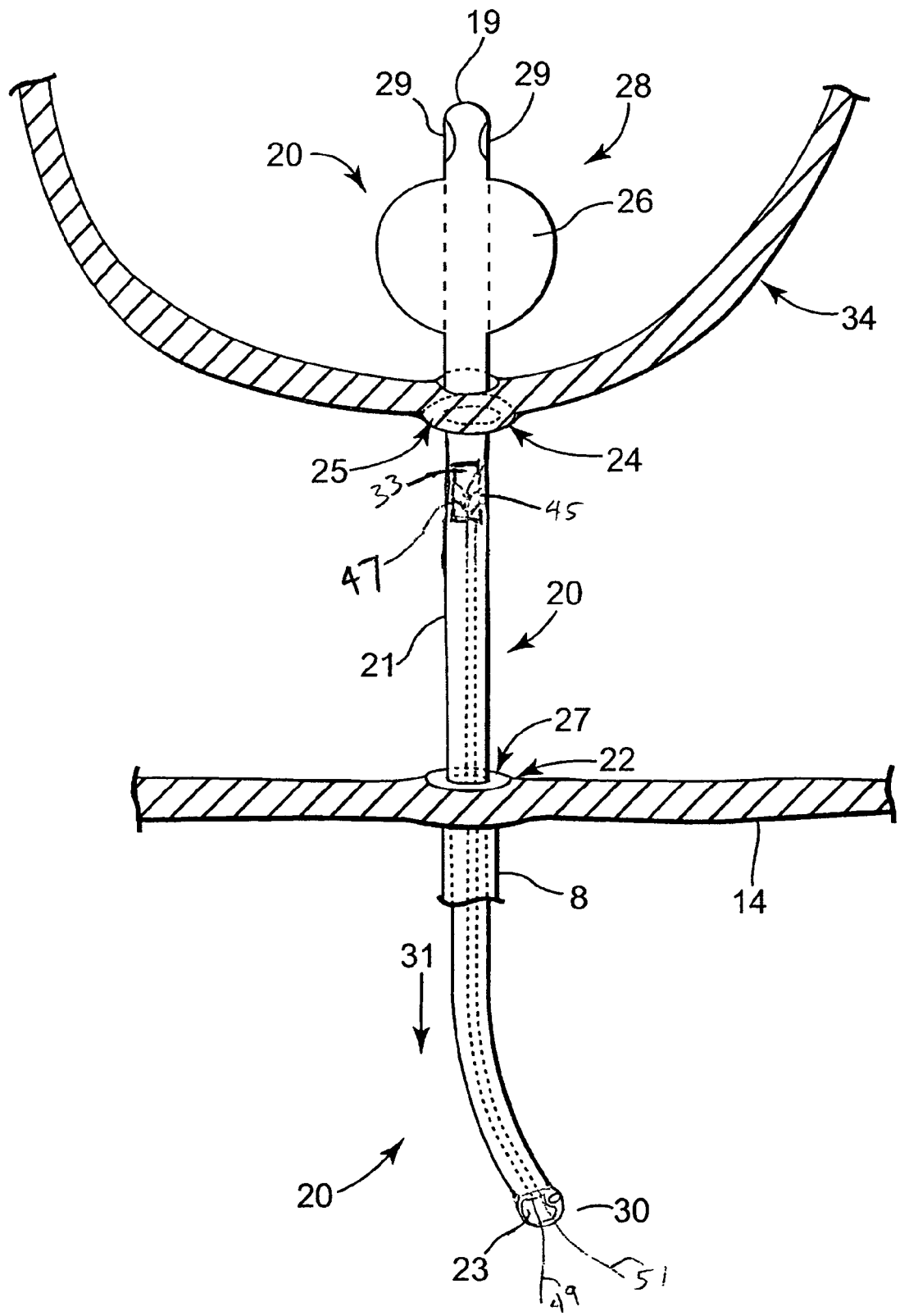
FIGS. 3 and 3a schematically illustrate an embodiment of an anastomosis device according to the invention.

In embodiments of devices according to FIGS. 2 and 2a, the anastomosis device 20, which in FIGS. 2 and 2a uses balloon 26 as a fixed, distal tissue approximating structure, additionally includes positionable tissue approximating structure. As an example, FIG. 3 illustrates positionable tissue approximating structure 45 included within hollow central channel 23 of elongate body 21. Positionable tissue approximating structure 45 can include features of a positionable tine structure as described herein, such as guide structure (not shown). As illustrated, positionable tissue approximating structure 45 includes tine support 33 and multiple extendable elongate tines 47 bound together as a single tine assembly. Tines 47 are connected to actuating mechanism 49, a wire extending to the proximal end of device 20. Tine support 33 is connected to positioning mechanism 51, a flexible wire extending to the proximal end of device 20.

During an anastomosis procedure, positionable tissue approximating structure 45 can be positioned as desired along a length of elongate body 21, for actuation, using positioning mechanism 51, e.g., such that tissue approximating structure 45 is at or below urethral stump 22. Positioning of tissue approximating structure 45 can be performed after positioning of urethral stump 22 against bladder neck 25, e.g., urethral stump 22 can be brought into contact with bladder neck 25, and positionable tissue approximating structure 45 can then be brought to the position of urethral stump 22, where tines 47 can be extended to maintain contact between the tissues 25 and 27.

Figure 3A:
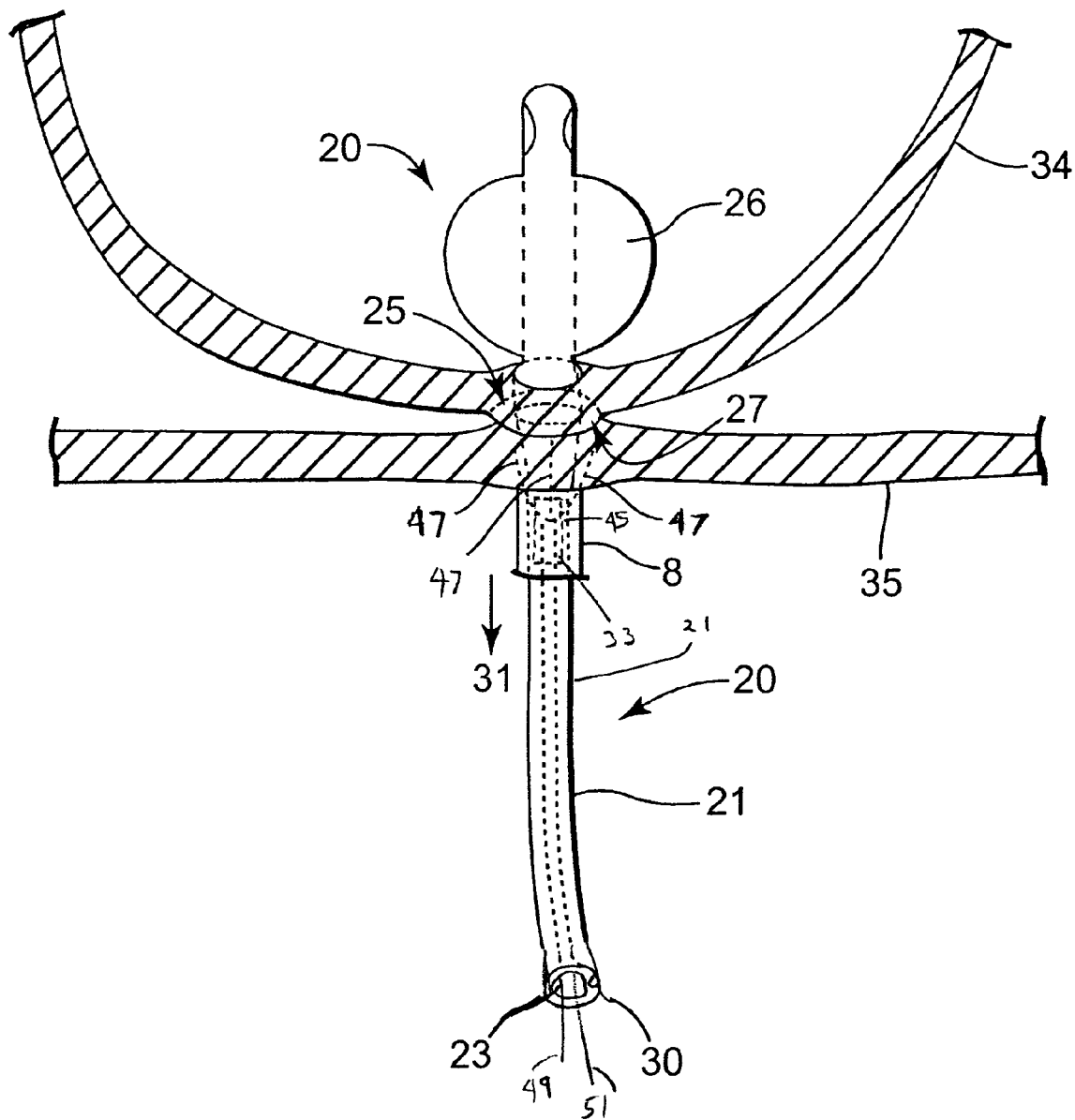

In more detail regarding an anastomosis procedure, while still referring to FIG. 3, the prostate (not shown) has been removed to leave a severed urethral stump tissue 22 (having surface 27) and opposing severed bladder neck 24 (having surface 25). Anastomosis device 20 is installed through urethra 8, urethral stump 22, and bladder neck 24. The device 20 comprises balloon 26 located at the distal end 28 of the device. The device also includes lumen 23 connecting drain apertures 29 to a proximal end of device 20. Balloon 26 is inflated and pressure (e.g., traction 31) can be applied through the length of device 20 to produce a pressure against the inside of bladder 34 (see FIG. 3a) from inflated balloon 26 to place the severed bladder neck tissue 25 in contact with severed urethral stump tissue 27. As shown in FIG. 3a, the surface 25 of the severed bladder neck can be aligned with the surface 27 of the severed urethral stump, around and along the axis of the catheter body 21. Also shown in FIG. 3a are tines 47 of tissue approximating structure 45, which are shown to be extended from tine support 33, through elongate body 21, to contact tissue of perineal floor 35. The severed urethral stump tissue 27 is pressured against the severed surface 25 of the bladder neck to allow healing together and reconnection of the two severed tissue surfaces. Optionally, not shown, the tines may extend through a slot (not shown) that extends along a length of elongate body 21, to allow the tines to be moved or adjusted after extension.

Figure 4:
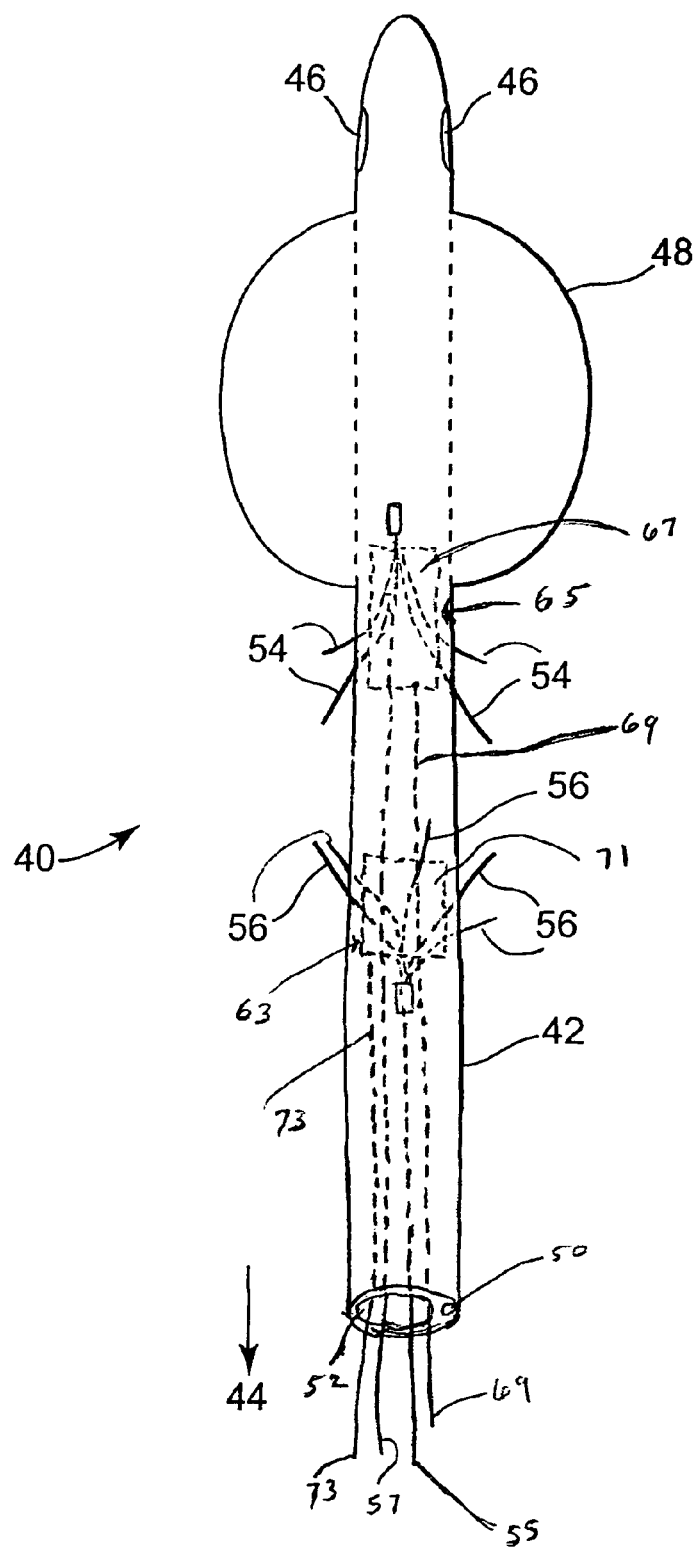

FIG. 4 shows another example of an anastomosis device of the invention, this embodiment including positionable distal tissue approximating structure 65 and opposing positionable proximal tissue approximating structure 63. Device 40 includes elongate body 42 with a proximal end 44 (not shown), a balloon 48, inflation lumen 50, and central passage 52. Inflation lumen 50 extends within the wall of elongate body 42 from the proximal end to the balloon 48, in fluid communication with the balloon 48, for inflating and deflating the balloon 48. Central passage or lumen 52 extends through body 42 of device 40, from the proximal end 44 (not shown), and communicates with drainage apertures 46. Distal tissue approximating structure 65 includes a set of distal tines 54 and distal tine support 67. Distal tissue approximating structure 65 can be positioned by moving distal positioning mechanism 69. Once distal tissue approximating structure 65 is in position, distal tines 54 can be extended through the wall of elongate body 42 and (as illustrated) in the general direction back toward the proximal end of the device 40 in a direction away from the distal end. Optional features of device 40 such as guide structure of distal tissue approximating structure 65 and proximal tissue approximating structure 63, are not shown, but may be included in the device as described herein, if desired.

Referring still to FIG. 4, positionable proximal tissue approximating structure 63 includes proximal tines 56 supported by proximal tine support 71, and is positioned on the proximal side of the device relative to balloon 48 and also toward the proximal side of the device relative to distal tines 54. Positionable proximal tissue approximating structure 63 can be moved lengthwise within body 42, to a desired position, during an anastomosis procedure, whereupon proximal tines 56 can be actuated to penetrate the wall of elongate body 42 to contact desired tissue for approximation. Proximal tines 56 are illustrated as extending in a direction toward the distal end of device 40 and away from the proximal end; thus, the distal and proximal tines are opposing. Each set of tines 54 and 56 can be independently remotely positioned and actuated, e.g., by using positioning mechanisms 69 (fixed to distal tine support 67) and 73 (fixed to proximal tine support 71), and actuating mechanisms 55 (for actuating proximal tines 56) and 57 (for actuating distal tines 54).

In use, when anastomosis device 40 of FIG. 4 is installed, balloon 48 is located inside of the bladder. See FIG. 4a. Distal tines 54 of distal tissue approximating structure 65 can be moved into a desired position along the body 42 so that when extended from body 42, distal tines 54 extend from body 42 to contact desired tissue for placing and preferably holding a severed tissue in place for healing. Likewise, proximal tines 56 of proximal tissue approximating structure 63 can be moved into a desired position along the body 42 so that when extended from the body 42, proximal tines 56 contact tissue for healing. As a specific example, distal tines 54 and proximal tines 56 can be positioned along body 42, after bladder and perineal floor tissues have been brought into contact, and then extended from body 42 such that distal tines 54 penetrate into tissue of the bladder and opposing proximal tines 56 penetrate into tissue of the perineal floor, the opposing tines applying pressure to hold the severed urethral stump against the bladder neck together for healing, while this embodiment of the anastomosis device also functions as a catheter to drain the bladder. See FIG. 4a.

FIG. 4b illustrates the device of FIGS. 4 and 4b used according to another variation of the inventive methods. As illustrated in FIG. 4b, tines 54 have been extended while inside of bladder 34, so that tines 54 do not contact bladder tissue at the time that tines 54 are extended. Tines 54 are then contacted to the inside surface of bladder tissue 34, and are pressed against that interior tissue surface, to splay out from body 42 without penetrating bladder tissue 34. In this configuration, the splayed tines can provide a uniform approximation around the circumference of the body 42, while balloon 48 performs the function of sealing the bladder from the site of anastomosis.

An alternate embodiment of a catheter device of the invention can include a fixed tissue approximating structure in the form of a balloon at a distal end, and a single positionable tissue approximating structure that includes, e.g., an assembly of multiple tines that can be positioned to be actuated and extended at a desired position along the length of a catheter body. The tines may extend through elongate apertures or slots that allow for lengthwise movement of the tines after the tines are extended to contact tissue. An example is shown in FIG. 5.

Figure 5:
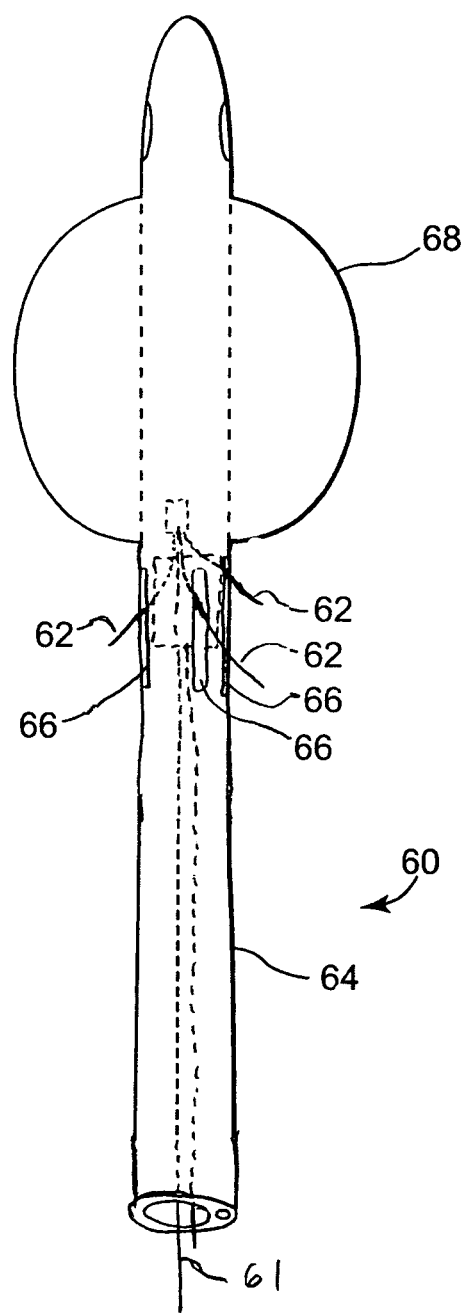
FIGS. 5 and 5a schematically illustrate an embodiment of an anastomosis device according to the invention.
Figure 5A:
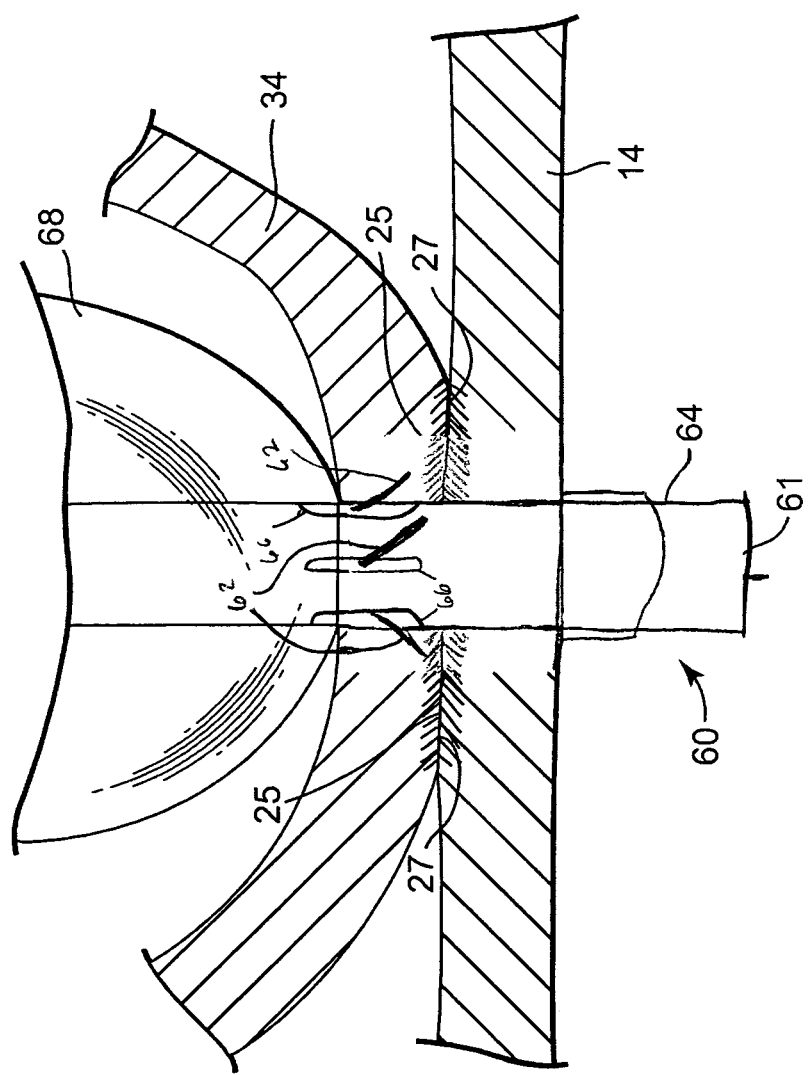

FIGS. 5 and 5a illustrate distal end 60 of an exemplary catheter device 75 of the invention, containing a single set of tines 62. In use, when device 75 is installed, balloon 68 is located inside of a bladder and tines 62 can be positioned at a position along the catheter body 64 to extend from the catheter body 64 to contact tissue for healing, e.g., tissue of the bladder wall (see FIG. 5a). As a result, the single set of tines 62 can be effective to hold a severed urethral stump in place next to severed bladder tissue. Tines 62 can be extended or retracted through elongate apertures 66 in catheter body 64, using actuating mechanism 61, and in coordination with positioning mechanism 63. In this embodiment, actuating mechanism 61 and positioning mechanism 63 run through a central lumen along a length of catheter body 64.

Still another embodiment of anastomosis device is shown in FIGS. 6 and 6a. Device 70 includes a balloon 78, e.g., as described elsewhere in this description, elongate body 71, and outer elongate body 72. Outer elongate body 72 includes positionable proximal tissue approximating structure that includes tines 74 that can be extended from a location at a distal end of outer elongate body 72. Each tine 74 extends within a channel (not shown) of the wall of outer elongate body 72, e.g., to a proximal end of outer elongate body 72 and to a proximal end of device 70. Tines 74 can be extended and retracted from the distal end of outer elongate body 72 by an actuating mechanism (not shown) that connects to each tine 74 at the proximal end of device 70. Outer elongate body 72 extends to a proximal end of device 70, allowing outer elongate body 72 to be moved along a length of elongate body 71. As such, outer body 72 can be moved along a length of body 71 to position tissue approximating structure, tines 74, at different locations along the length of elongate body 71. Overall, tines 74 are positionable tissue approximating structure that can be positioned by movement of outer elongate body 72 along a length of elongate body 71. Once positioned as desired by movement of outer elongate body 72, tines 74 can be extended or retracted as desired, to contact, move, or hold tissue for healing. As desired, tines 74 can be extended either before or after contacting tissue, e.g., to hold tissue in place for healing, to manipulate tissue into position for healing, or both.

Referring to FIG. 6a, device 70 can be installed to locate balloon 78 inside of a bladder 34. Outer body 72 can be positioned, for example, along elongate body 71 to a location that will allow tines 74 to be extended from outer body 72 to contact tissue for healing, e.g., tissue of the perineal floor 14. Tines 74 can be extended or retracted either before or after perineal floor is brought into contact with bladder 34. Thus, by combined movement of outer body 72 and actuation of tines 74, positionable tines 74 can be used to contact tissue of perineal floor 14 and bring the tissue into contact with tissue of bladder 34, to hold tissue of perineal floor 14 in contact with tissue of bladder 34, or to do both. The surface of severed bladder neck tissue 25 can be aligned with the surface 27 of severed urethral stump 22, around and along elongate body 71.

Still another embodiment of anastomosis device is shown in FIGS. 7 and 7a. Device 80 includes a balloon 82, e.g., as described elsewhere in this description, elongate body 84, and outer elongate body 86. Outer elongate body 86 includes positionable proximal tissue approximating structure 88, in the form of an inflatable balloon located toward the distal end of outer elongate body 86. Balloon 88 communicates through a lumen within the wall of outer elongate body 86, e.g., extending from balloon 88 to a proximal end of outer elongate body 86 and to a proximal end of device 80. Balloon 88 can be inflated and deflated to extend from the distal end of outer elongate body 86 by flow of fluid through inflation lumen 90. Outer elongate body 86 extends to a proximal end of device 80, allowing outer elongate body 86 to be moved along a length of elongate body 84. As such, outer elongate body 86 can be moved along a length of body 84 to position the proximal, positionable tissue approximating structure, balloon 88, at different locations along a length of elongate body 84. Overall, balloon 88 is positionable tissue approximating structure that can be positioned by movement of outer elongate body 86 along a length of elongate body 84. Once positioned as desired by movement of outer elongate body 86, balloon 88 can be extended or retracted as desired, to contact, move, or hold tissue for healing. As desired, balloon 88 can be extended either before or after tissue is moved into place during an anastomosis procedure.

Referring to FIG. 7a, device 80 can be installed to locate balloon 82 inside of a bladder 34. Tissue of perineal floor 14 can be positioned to contact tissue of bladder 34, by movement of perineal floor along elongate body 84. The surface of severed bladder neck tissue 25 can be aligned with the surface 27 of severed urethral stump 22, around and along elongate body 84. Balloon 88 can be inflated at a desired time during the procedure relative to movement of perineal floor 14 to contact bladder 34. Thus, by combined movement of outer body 86 and inflation of balloon 88, positionable tissue approximating structure balloon 88 can be used to contact tissue of perineal floor 14 and bring the tissue into contact with tissue of bladder 34, to hold tissue of perineal floor 14 in contact with tissue of bladder 34, or to do both.

Alternate embodiments of anastomosis devices (and related methods) will be useful according to this description, as will be appreciated by those of skill, even if not specifically illustrated or described. For example, combinations of the above described features of anastomosis devices and the various described forms of positionable tissue approximating structure, will be understood to be useful, in various combinations, to function as tissue approximating structure, optionally while functioning as a catheter.

Specific embodiments of anastomosis devices according to the invention and their componentry may be made of materials normally used and known to be useful for anastomosis or catheter devices, or future developed materials, especially including known or future developed materials that are relatively inert and biocompatible. For example, an elongate body of a device may be prepared from a flexible plastic or polymeric material. Examples of presently understood materials that may be useful for an elongate body can include silicones, latex, rubbers, polyurethanes, and combinations of these or other materials, of desired and useful thicknesses. A tissue approximating structure can be made from these or other materials, including relatively rigid plastics, polymers, or metals, or from flexible materials for balloons. Examples of metals include stainless steel, nitinol, titanium, tantalum, as well as alloys or combinations of these materials.

According to certain embodiments of the invention that include tines that extend through a solid wall of an elongate body, the elongate body can be prepared from a material, and can have a thickness, that will allow a tine or other elongate tissue approximating structure to puncture the wall of the elongate body when the tissue approximating structure is actuated. Also preferably, the material can be sufficiently flexible and resilient, and of a thickness, to allow the wall of the structure to be pierced by a tine upon actuation of the tine, and additionally allow the tine to be retracted, with the wall of the body re-sealing upon retraction of the tine.

The anastomosis device, in addition to the foregoing, may also include other mechanisms or features, as will be appreciated by those of skill. As one example of a specific feature that may be incorporated into an embodiment of the invention, a positioning or actuating mechanism for a tissue approximating structure may be removable at an exterior portion of the device. For example, a positioning or actuating mechanism may extend through an elongate body through an end or through a port at the proximal end of the device. The mechanism or a portion thereof may be removably attached to the device and the tissue approximating structure, so that a surgeon using the device can operate the tissue approximating structure while the positioning or actuating mechanism is attached, during a surgical procedure, and the actuating or positioning mechanism may be removed following the procedure to avoid inadvertent manipulation by the patient during the healing period, during which the device is still installed in the patient. When the time comes to remove the device, the mechanism may be re-attached externally to uninstall the device.

In general, a device as described can be used during any type of anastomosis procedure, specifically including urethral anastomosis procedures such as those associated with a radical prostatectomy, e.g., vesico-urethral anastomosis, with the anastomosis device functioning to approximate tissue while the catheter features function to remove urine from the bladder after the procedure. By ordinary urethral anastomosis methods, and according to the inventive methods described herein, an anastomosis device can be used by inserting a distal end of the elongate flexible body through the urethra and into the bladder. A portion of the distal end becomes located inside of the bladder where the balloon can be inflated and where the drainage lumen can be positioned to drain the bladder and prevent the bladder from becoming full and pressurized during and subsequent to the procedure. The bladder can preferably be drained of urine during the procedure and during the healing period following the procedure, because urine is preferably kept away from the site of anastomosis to facilitate healing, and also to prevent urine from creating pressure within the bladder.

A typical Foley catheter can include a drainage lumen and an inflation lumen for inflating and deflating the balloon. The balloon is normally deflated until properly positioned in a bladder. Once the device is positioned as desired, the inflation lumen delivers fluid to inflate the balloon. The inflated balloon can be used to hold the device in place, and, according to certain methods of the invention, can be used to draw the bladder and bladder neck toward the urethral stump and to hold the bladder in that position during healing of the bladder neck to urethral stump.

Figure 8:
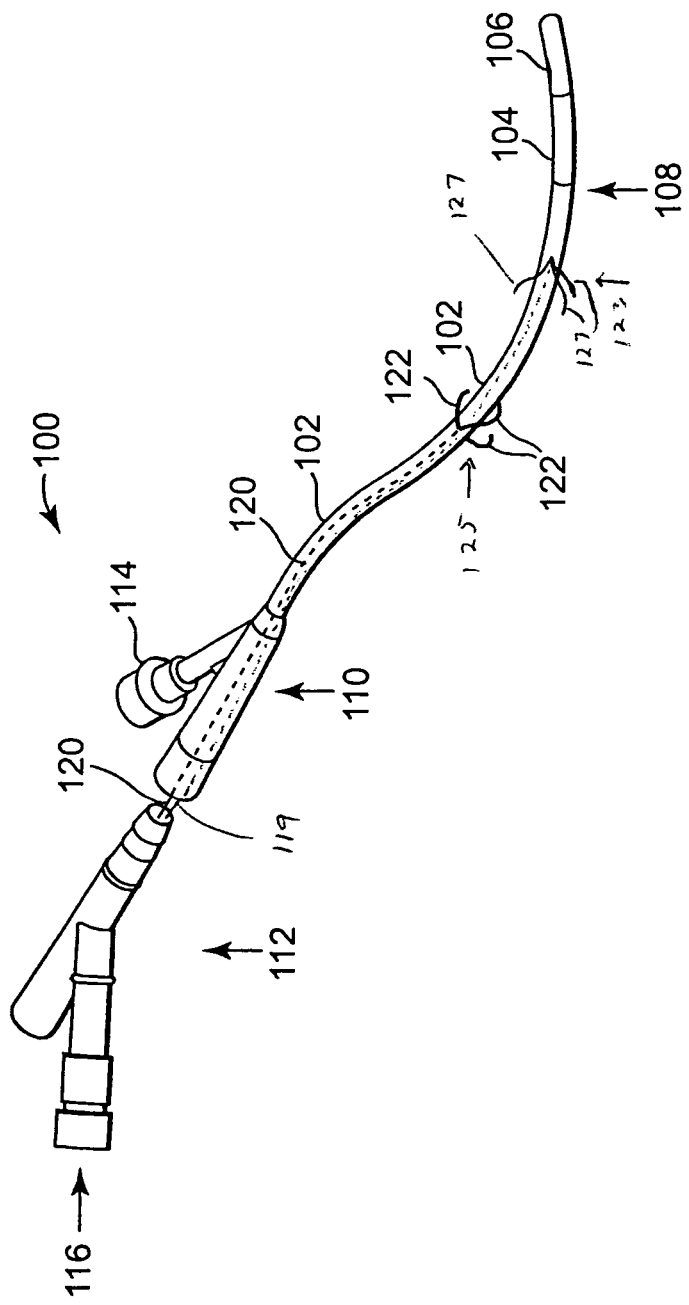
FIG. 8 schematically illustrates an embodiment of an anastomosis device of the invention.

FIG. 8 shows a single example of a modified-Foley-catheter-type anastomosis device according to the invention. Device 100 includes distal end 108, elongate catheter body 102, balloon 104, and drainage aperture 106. Positionable tissue approximating structure can be located inside hollow body 102, as illustrated, to be moved and positioned to desired locations between the proximal and distal ends of the device. The location along a length of the elongate body can be selected depending on the particular procedure being performed. For example, in performing an end-to-end urethral anastomosis procedure, a location mid-way along the elongate body may be used. For a vesico-urethral procedure, a position closer to balloon 104 may be useful. Two positionable tissue approximating structures are illustrated as components of device 100: proximal tissue approximating structure 125, and distal tissue approximating structure 123, each including a set of tines, 122 and 127, respectively. (Detailed features of the positionable tissue approximating structures as described herein, while optionally included in each of the illustrated tissue approximating structures, are not specifically shown.) Each of the positionable tissue approximating structures may be independently positioned and actuated using their respective positioning mechanisms (119 and 120), and actuating mechanisms (not specifically shown).

Still referring to FIG. 8, device 100 includes proximal end 110 that includes a port 114 that can be connected to a desired attachment (not shown) useful to operate device 100 during an anastomosis procedure, e.g., to inflate a balloon, to connect to a drainage lumen, etc. Examples of such proximal end attachment configurations are well known, and such known or future developed proximal ends and attachments will be understood to be useful according to devices and methods of the invention. In the illustrated embodiment, proximal end 110 includes a port 114 that may connect to a lumen (not shown) such as an inflation lumen for balloon 104 or a drainage lumen from aperture 106. Another port, 116, of attachment 112, can also be used with an inflation lumen or a drainage lumen. One or more wires 119 and 120 can connect to tissue approximating structures 125 and 123, e.g., as a positioning mechanism, for positioning tines 122 and tines 127. (Actuating mechanisms for each tissue approximating structure are not shown.) Wires 119 and 120 may be attached to an additional portion of a positioning mechanism, such as a turnable knob or a lever (not shown), etc., that can be moved or rotated to position tines 122 or 127. Other variations of these features of the illustrated attachment and proximal end will be understood by those of skill, and may be used in combination with the features of the present invention. For example, while proximal tissue approximating structure 125 includes tines 122 and not a balloon, a balloon may be used as an alternate to tines 125 with modification of the overall device to allow for positioning and actuation of the balloon.

Generally, a method of the invention can include a step of performing anastomosis by a known or future developed technique. One example is anastomosis following a prostatectomy by any of a retropubic technique, a laparoscopic technique, or a transperineal technique. These techniques leave a bladder neck and a urethral stump for re-attachment. Other types of anastomosis of severed body lumens, e.g., other than a urethra, will be understood to be also performed according to the present disclosure. Prior urethral anastomosis techniques may use sutures or other mechanisms or structures that are separate from a catheter to re-attach severed tissues. The use of sutures or other such separate mechanisms or structures is preferably not necessary, and most preferably avoided, according to methods of the invention.

In terms of urethral anastomosis, a distal end of an anastomosis device may be installed during a prostatectomy procedure, e.g., up to the perineal floor, or may be installed to that point afterward. Following removal of the prostate, the elongate body of the distal end of the device can be passed through the urethral stump and then through the bladder neck. From there, the technique can include inflating a balloon inside of the bladder and positioning and actuating tissue approximating structure (e.g., tines or a balloon) to place the severed tissue surfaces of the urethral stump and the bladder neck into contact for healing. Positionable tissue approximating structure can be moved at any time before or during an anastomosis procedure, according to various embodiments of the invention, and before or after any particular step of an anastomosis procedure. A preferred step can also be to close the bladder neck to a desired size via a purse-string suture.

Common to vesico-urethral techniques can preferably be to carefully avoid damaging sensitive tissues near the bladder neck and urethral stump. Specifically, ureters are proximal to the bladder neck and should not be contacted. Proximal to the urethral stump are sensitive nerves and a sphincter. Some of these tissue structures are generally regarded as being at the 5 o'clock and 7 o'clock positions of the bladder neck and the urethral stump. Advantageously, devices and methods of the invention can afford significant opportunity to identify the location of these tissues, and position and re-position tissue approximating structure to avoid sensitive tissue. As yet an additional feature of devices of the invention, markings can be made along a length of the exterior surface of the catheter body, e.g., at the location of apertures from which elongate tissue approximating structures extend. A surgeon can view these markings when positioning the catheter body relative to a urethral stump and bladder neck, to avoid potential damage to sensitive tissue locations. Also in preferred embodiments, elongate tissue approximating structures such as tines or needles can be constructed and located to facilitate avoidance of sensitive tissues, such as by providing a set of three tines that radiate from a cross section of a catheter body at approximately 120 degree angles apart from each other. Still other embodiments can use balloons as tissue approximating structure, which can further reduce the possibility of damaging sensitive tissues.

Examples of steps to install tissue approximating structures can be described by reference to the figures. Referring to FIGS. 2 and 2a, an example of steps for using tissue approximating structure of an embodiment of an anastomosis device shown, can be as follows. Following inflation of balloon 26 inside of bladder 34, the bladder is pulled against perineal wall 14 (see FIG. 2a). Severed bladder neck surface 25 contacts severed urethral stump tissue 27, to allow healing with the device 20 installed. Optionally and preferably, but not shown in FIGS. 2 and 2a, a positionable tissue approximating structure (e.g., balloon or tines) may be moved into position proximal to perineal floor 14, then actuated to contact tissue of the perineal floor 14, to produce pressure from the perineal floor 14 against the bladder neck 24 and balloon 26.

Figure 4A:
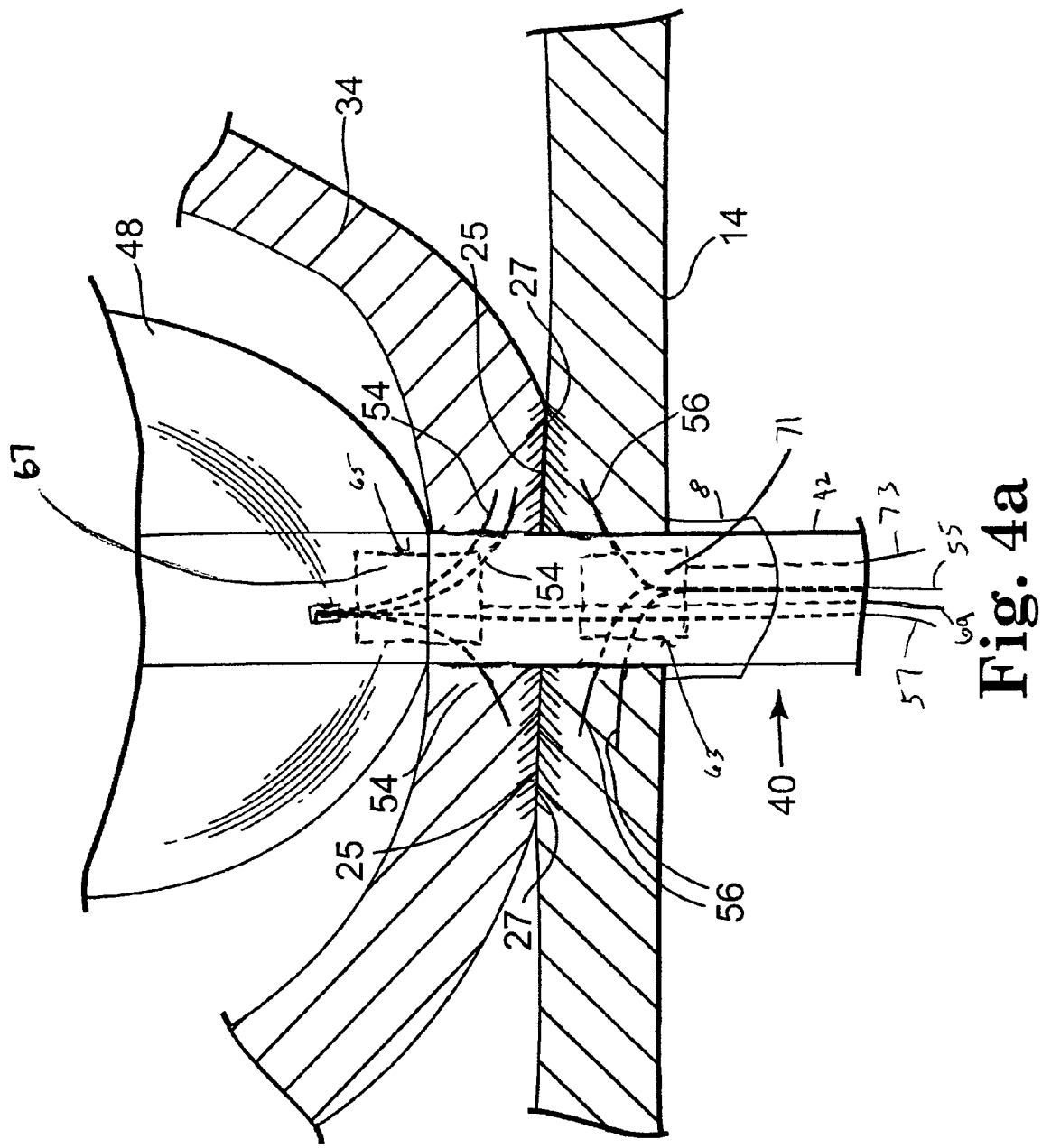

As another example, referring to FIG. 4a, following inflation of balloon 48 inside of bladder 34, the bladder can be pulled against perineal wall 14. Severed bladder neck surface 25 contacts severed urethral stump tissue 27. Prior to or after pulling the bladder 34 to contact the perineal wall 14, positionable distal approximating structure that includes tine support 67 and tines 54 can be positioned near bladder tissue 34, using distal positioning mechanism 69. Distal tines 54 can be extended from body 42 to contact bladder tissue 34, carefully avoiding ureters (not shown) optionally by reviewing the position of distal tines 54 and repositioning or retracting and re-inserting distal tines 54 as necessary, either by retraction of the tines or by adjusting the position of the elongate body 42 or positionable distal tine support 67 relative to the bladder tissue 34. Distal tines 54 may penetrate into or through bladder tissue 34, as desired. After bringing the bladder to contact the perineal wall 14, positionable proximal tissue approximating structure, including tine support 71 and proximal tines 56, can be positioned as desired using proximal positioning mechanism 73. Proximal tines 56 can be actuated to extend from body 42 to contact perineal wall 14. Severed bladder neck surface 25 contacts severed urethral stump tissue 27, and the severed tissue surfaces can be held together to allow healing while device 40 remains installed. Upon completion of the healing process, tines 54 and 56 can be retracted back into body 42 and device 40 can be removed.

As still another example, referring to FIG. 5a, following inflation of balloon 68 inside of bladder 34, bladder 34 is pulled against perineal wall 14. Severed bladder neck surface 25 contacts severed urethral stump tissue 27. Tissue approximating structure in the form of tines 62 can be extended through elongate slots 66, to contact or penetrate bladder tissue 34. During or after positioning and actuating tines 62, tines 62 may be moved and adjusted, e.g., to adjust the position of the tines relative to device 60 and thereby adjust the position of tissue. Severed bladder neck surface 25 contacts severed urethral stump tissue 27, to allow healing, while the anastomosis remains installed. Upon completion of the healing process, tines 62 are retracted back into the catheter body 64, by use of actuating mechanism 61, and the device can be removed.

FIG. 6a illustrates certain details of another embodiment of a method of the invention. Following inflation of balloon 78 inside of bladder 34, the bladder 34 can be pulled against perineal wall 14. Severed bladder neck surface 25 contacts severed urethral stump tissue 27. Outer body 72 of device 70 can be moved to position the positionable proximal tissue approximating structure, tines 74, along a length of elongate body 71, as desired relative to perineal floor 14. This can be done before, during, or after, perineal floor 14 is moved into contact with tissue of bladder 34. Proximal tissue approximating structure, tines 74, proximal to perineal floor 14, can be extended to penetrate into perineal floor 14, and, optionally further penetrate into bladder 34. Severed bladder neck surface 25 contacts severed urethral stump tissue 27, to allow healing, while the anastomosis remains installed. Upon completion of the healing process, tines 74 are retracted back into the outer elongate body 72, and device 70 can be removed.

FIG. 7a illustrates certain details of another embodiment of a method of the invention. Following inflation of balloon 82 inside of bladder 34, bladder 34 can be pulled against perineal wall 14. Severed bladder neck surface 25 contacts severed urethral stump tissue 27. Outer body 86 of device 80 can be moved to position the positionable proximal tissue approximating structure, balloon 88, along a length of elongate body 84, as desired relative to perineal floor 14. This can be done before, during, or after, perineal floor 14 is moved into contact with tissue of bladder 34. Proximal tissue approximating structure, balloon 88, proximal to perineal floor 14, can be inflated within urethra 8 to contact and place pressure on the underside of perineal floor 14. Severed bladder neck surface 25 contacts severed urethral stump tissue 27, to allow healing, while the anastomosis remains installed. Upon completion of the healing process, balloons 82 and 88 can be deflated and device 80 can be removed.

Figure 9A:
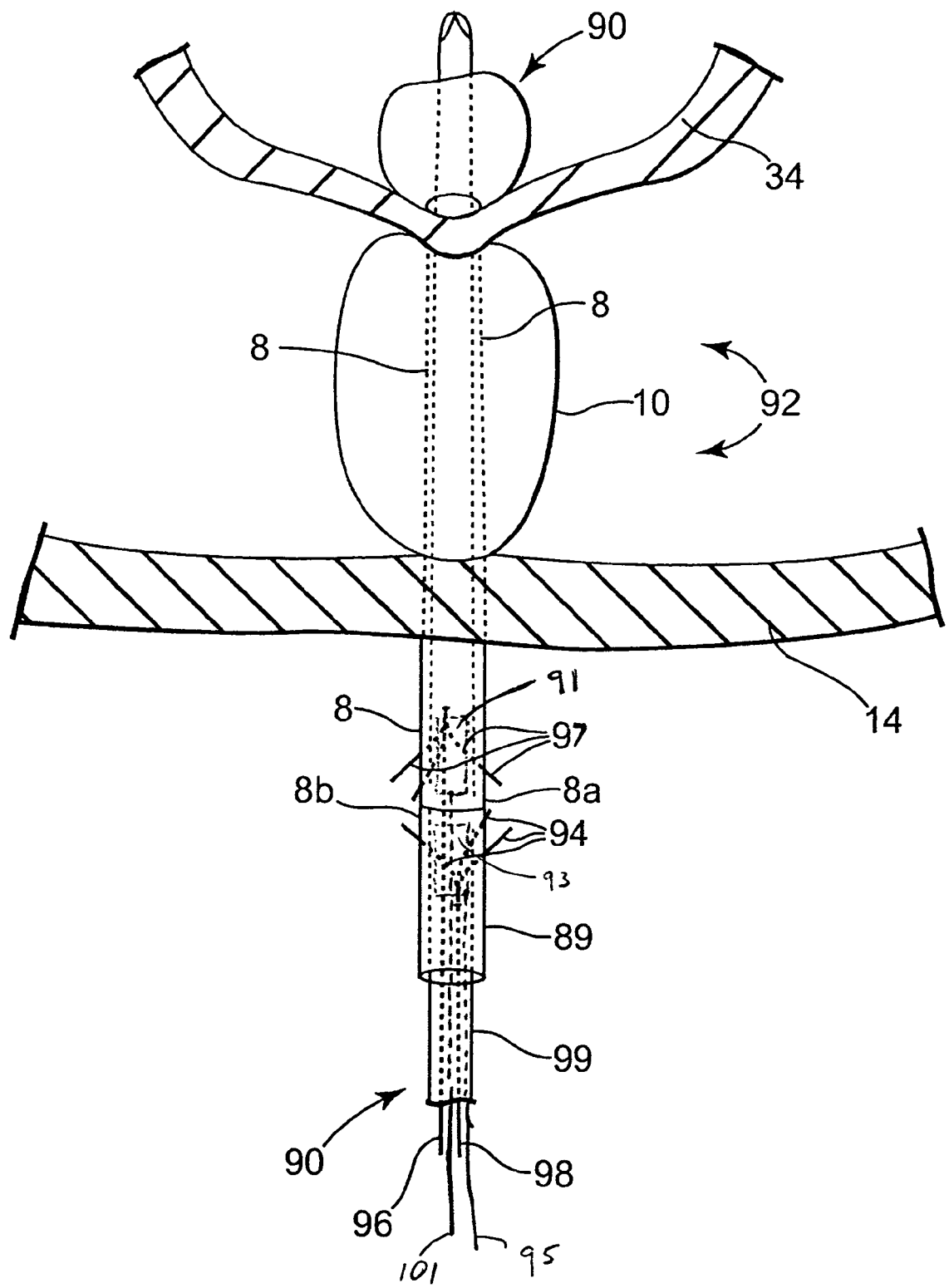

FIGS. 9 and 9*a* show still additional embodiments of inventive methods relating to a urethral anastomosis procedure below the perineal floor. FIG. 9 illustrates device 92 having distal end 90 installed through perineal floor 14 and into bladder 34, through urethra 8, which passes through prostate 10. This procedure does not include removal of the prostate, but instead relates to severing and re-attaching urethra 8 at a point below perineal wall 14, e.g., re-attaching severed urethra portions 8*a* and 8*b*. According to the illustration, proximal tines 94 of a positionable proximal tissue approximating structure (that also includes tine support 93), and distal tines 97 of a positionable distal tissue approximating structure (that also includes tine support 91), can be used to place surfaces of severed urethra portions 8*a* and 8*b* together and hold them together for healing (see FIG. 9*a*). Specifically, proximal tines 94 and distal tines 97 together can be positioned and actuated to hold tissues 8*a* and 8*b* in contact, in opposition. Each set of tines is independently positionable using distal position mechanism 101 and proximal positioning mechanism 95. Each set of tines is also independently actuatable by use of actuating mechanisms 96 and 98.

FIG. 9*a* illustrates the extended distal and proximal sets of tines, 94 and 97, extending into opposing portions of severed urethra 8, and holding the severed tissue portions 8*a* and 8*b* in contact for healing. The tines contact, optionally move, and hold the tissue portions 8*a* and 8*b* together for healing. The installed device also includes a balloon in bladder 34 and a drainage lumen means that function together to cause urine to pool in the bladder and drain from the bladder. Thus, the illustrated device may be left installed, including the tissue approximating structure, during the healing period. As will be appreciated, other embodiments of the device may also be used in an end-to-end anastomosis procedure, such as, for example, a device that includes only a single tine support structure that positions and assists in actuating two sets of positionable tissue approximating structures, such as is illustrated in FIG. 16.

Figure 9B:
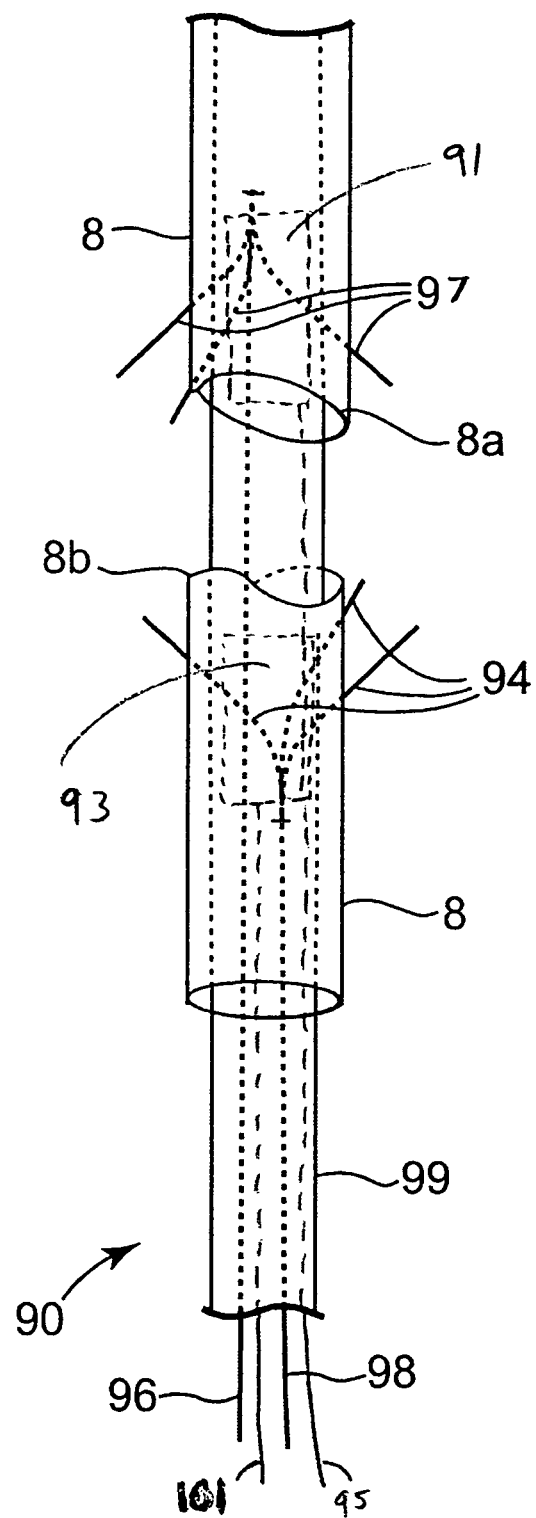
Figure 9C:
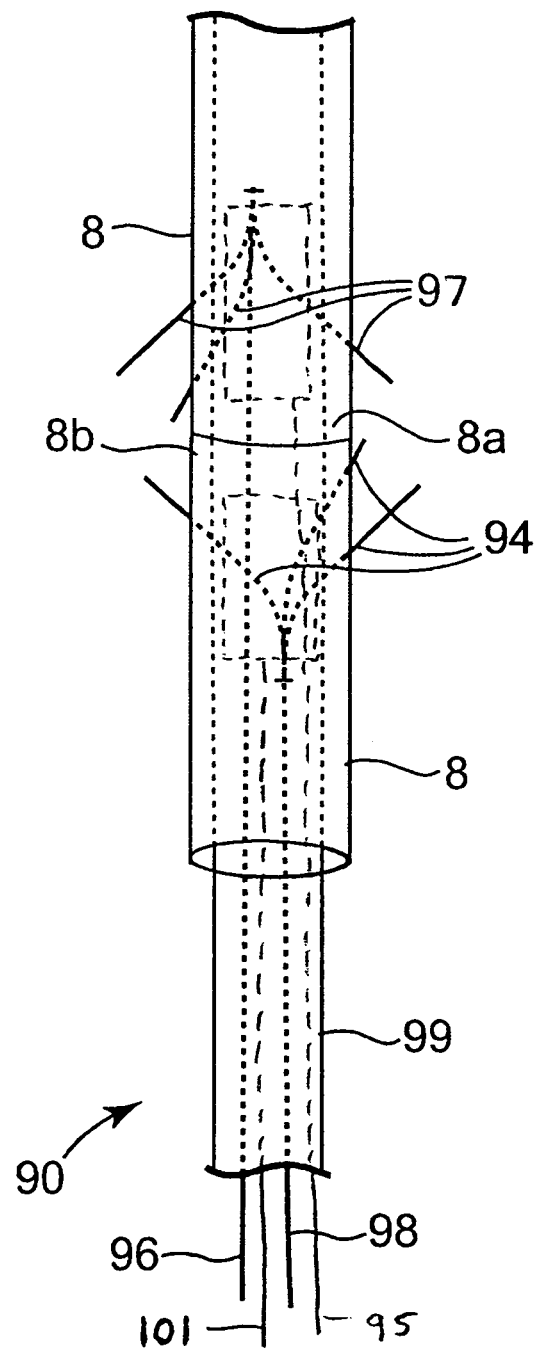

FIGS. 9*b* and 9*c* are close-up illustrations of devices and tissue approximating structures of FIGS. 9 and 9*a*, respectively, for clarity. As is illustrated in close-up FIGS. 9*b* and 9*c*, tines 94 and 97 can be extended from body 99 to penetrate into and optionally through urethral tissue 8. The opposing severed urethral tissues are brought together (optionally with the assistance of the opposing tines) and are held together as shown in FIG. 9*c*, preferably for a time sufficient to cause healing together of the severed tissues while the anastomosis device is installed and functions to drain urine from the bladder.

Embodiments of anastomosis devices as described herein can remain installed in a patient during the time required for healing of two tissue surfaces together. In embodiments of devices that can be used as catheters, e.g., during urethral anastomosis procedures, a distal balloon located in the bladder can remain inflated to prevent urine from passing through the bladder neck. The healing period can be considered the time period taken for severed tissue to achieve a water tight anastomosis. The healing period can depend on many factors such as the type of operation and the patient, and can take, e.g., from possibly as little as one or two days, up to possibly two months, with periods of from one to four weeks being sometimes typical.

While a catheter device of the invention is installed, urine accumulates and pools inside of the bladder and can be drained from the bladder through drainage apertures and a drainage lumen within the device, flowing to the proximal end of the device for collection. Such embodiments of the inventive devices and methods offer the advantage of providing a single anastomosis device that functions to allow severed tissue surfaces to heal together by use of the tissue approximating structure, without sutures, while at the same time providing a draining mechanism. The advantage of not requiring sutures for holding the severed tissues together or for healing can offer cost savings and eliminate complications by significantly reducing procedure time, thus reducing costs, and also reducing the length of time a patient is anesthetized. Additionally, the procedure does not leave sutures behind, but instead, the tissue approximating structures of the anastomosis device can be retracted or deflated, and the device can be removed after healing.

Following is one series of more detailed exemplary steps useful according to the methods of the invention, for using an embodiment of inventive anastomosis device to perform a prostatectomy. Other embodiments of devices, as specifically described herein or consistent with the present overall description, will be appreciated.

1. Perform a radical prostatectomy by any method such as retropubic, laparoscopic, or transperineal, until prior to the vesico-urethral anastomosis. The following description is in the context of a retropubic radical prostatectomy, and with reference to an embodiment of an inventive device as illustrated at FIGS. 4 and 4*a*.
2. Close the bladder neck to the desired size via a pursestring suture.
3. The anastomosis device (AD) can be inserted into the bladder prior to the suturing to help determine the desired size or the bladder can be sutured independently.
4. Insert the AD through the meatus until it exits the urethral stump in the open abdomen.
5. Pull the AD until enough length has been exposed to reach the bladder.
6. Insert the AD into the bladder and inflate the balloon.
7. Position and extend distal tines of the AD to contact bladder tissue, and visually ensure that the tines do not penetrate the ureters of the bladder. This can be facilitated by extending and retracting the tines and seeing the "bump" form on the exterior wall of the bladder. The AD may also have visual markers on the external wall of the AD proximal to the distal tines, to mark the location of the tines.
8. The bladder can then be lowered to the perineal floor by releasing the traction on the bladder and physically moving the bladder down by hand toward the perineal wall, while lightly maintaining tension on the AD.
9. Once the bladder has been drawn to contact the urethral stump, a light tension can be placed on the AD while the proximal tines are positioned and extended into the perineal floor. (Alternately, if the proximal tissue approximating structure includes a balloon instead of tines, the balloon may be positioned and inflated.)
10. The bladder can then be filled using the drainage port on the AD and the anastomosis site can be checked for leaks.
11. If a leak is experienced the AD can be repositioned until the desired performance is reached.

12. The AD can remain in place for a time depending on the healing needs of the individual patient.

The invention claimed is:

1. An anastomosis catheter device comprising
a flexible elongate body comprising a proximal end, a distal end, and a body wall extending along a length of the flexible elongate body,
positionable tissue approximating structure that can be positioned length-wise along the elongate body and that can be extended and retracted from the body wall over a range of positions along the length of the elongate body to contact tissue for anastomosis,
an inflatable balloon at the distal end and an inflation lumen extending from the proximal end to the balloon, and
a drainage lumen extending from a drainage aperture at the distal end to the proximal end.

2. The device of claim 1 wherein, when the device is installed in a body having a prostate removed, with the balloon in a bladder, the positionable tissue approximating structure is capable of contacting tissue selected from tissue of a bladder, tissue of a perineal wall, urethral tissue, and combinations of these.

3. The device of claim 1 wherein the positionable tissue approximating structure comprises a tine assembly that is positionable within a length of the elongate body, the tines being capable of extending from the elongate body to contact tissue for approximation.

4. The device of claim 3 wherein the positionable tissue approximating structure is connected to
a positioning mechanism extending from the positionable tissue approximating structure, through the elongate body, to a proximal end of the device, and
an actuating mechanism extending from the positionable tissue approximating structure, through the elongate body, to a proximal end of the device.

5. The device of claim 4 wherein the positioning mechanism is selected from a wire and a hollow tube.

6. The device of claim 1, comprising a hollow central channel, the positionable tissue approximating structure comprising
distal positionable tissue approximating structure within the hollow central channel of the elongate body, the distal positionable tissue approximating structure being capable of extending from the elongate body to contact tissue for anastomosis, and
proximal positionable tissue approximating structure within the hollow central channel of the elongate body, proximal positionable tissue approximating structure being capable of extending from the elongate body on the proximal side of the distal positionable tissue approximating structure.

7. The device of claim 6 wherein
the distal positionable tissue approximating structure comprises a tine support and a tine assembly, and
the proximal positionable tissue approximating structure comprises a tine support and a tine assembly.

8. The device of claim 1, wherein the positionable tissue approximating structure extends through the body wall.

9. An anastomosis device comprising
an elongate body comprising a body wall and a lumen, each extending along a length of the elongate body, the lumen comprising a hollow central channel,
positionable tissue approximating structure that can be positioned length-wise along the elongate body and that can be extended and retracted from the body wall over a range of positions along the length of the elongate body to contact tissue for anastomosis, comprising
a distal positionable tissue approximating structure within the hollow central channel of the elongate body, the distal positionable tissue approximating structure being capable of extending from the elongate body to contact tissue for anastomosis, and comprising a tine support and a tine assembly, and
a proximal positionable tissue approximating structure within the hollow central channel of the elongate body, the proximal positionable tissue approximating structure being capable of extending from the elongate body on the proximal side of the distal positionable tissue approximating structure, and comprising a tine support and a tine assembly, and
wherein the distal postionable tissue approximating structure and the proximal positionable tissue approximating structure can be positioned independently inside the elongate body and each tine assembly can be independently actuated to extend from the elongate body.

10. An anastomosis catheter comprising
an elongate body comprising a body wall and a lumen, each extending along a length of the elongate body, the lumen comprising a hollow central channel,
positionable tissue approximating structure that can be positioned length-wise along the elongate body and that can be extended and retracted from the body wall over a range of positions along the length of the elongate body to contact tissue for anastomosis, comprising:
a distal positionable tissue approximating structure within the hollow central channel of the elongate body, the distal positionable tissue approximating structure being capable of extending from the elongate body to contact tissue for anastomosis,
a proximal positionable tissue approximating structure within the hollow central channel of the elongate body, the proximal positionable tissue approximating structure being capable of extending from the elongate body on the proximal side of the distal positionable tissue approximating structure,
an inflatable balloon at a distal end of the device,
an inflation lumen extending from the balloon to a proximal end of the device, and
a drainage lumen extending from a drainage aperture at the distal end to a drainage port at the proximal end of the device.

11. A method of performing anastomosis, the method comprising
inserting a portion of an anastomosis device into a body lumen, the anastomosis device comprising
an elongate body comprising a body wall and a lumen, each extending along a length of the elongate body, and
positionable tissue approximating structure that can be positioned length-wise relative to the elongate body and that can be extended and retracted from the body wall over a range of positions along the length of the elongate body,
moving the positionable tissue approximating structure along a length of the elongate body,
extending the positionable tissue approximating structure from a location along the length of the device, and
using the positionable tissue approximating structure to hold severed tissue during anastomosis.

12. The method of claim 11 wherein the positionable tissue approximating structure comprises tines.

13. The method of claim 11 wherein the method is a urethral anastomosis and the method comprises inserting a portion of the anastomosis device into the body lumen, wherein the lumen is a urethra and the anastomosis device comprises
   an inflatable balloon at a distal end,
   an inflation lumen extending from the balloon to a proximal end of the device, and
   a lumen extending from a drainage aperture at the distal end of the device to a drainage port at the proximal end of the device,
inflating the balloon in the bladder,
moving the positionable tissue approximating structure to a location proximal to a severed tissue and extending the positionable tissue approximating structure, and
using the tissue approximating structure to maintain the approximation of the severed tissue.

14. The method of claim 13 wherein the positionable tissue approximating structure comprises tines.

15. The method of claim 11 wherein the method is a urethral anastomosis and the method comprises
   inserting a portion of the anastomosis device into the body lumen, wherein the lumen is a urethra and the anastomosis device comprises
      an inflatable balloon at a distal end,
      an inflation lumen extending from the balloon to a proximal end of the device, and
      a lumen extending from a drainage aperture at the distal end of the device to a drainage port at the proximal end of the device,
   inflating the balloon in the bladder,
   moving the positionable tissue approximating structure to a location proximal to a severed tissue and extending the positionable tissue approximating structure, and
   using the tissue approximating structure to maintain the approximation of the severed tissue.

16. The method of claim 15 comprising using the tissue approximating structure to hold the urethral stump in contact with the bladder neck for a time sufficient to allow the urethral stump and the bladder neck to heal together.

17. The method of claim 11 wherein the positionable tissue approximating structure extends through the body wall.

18. An anastomosis catheter comprising
   an elongate body comprising a body wall and a lumen, each extending along a length of the elongate body,
   positionable tissue approximating structure that can be positioned length-wise along the elongate body and that can be extended and retracted from the body wall over a range of positions along a length of the elongate body to contact tissue for anastomosis,
   an inflatable balloon at a distal end and an inflation lumen extending from a proximal end to the balloon, and
   a drainage lumen extending from a drainage aperture at the distal end to the proximal end.

19. The device of claim 18 wherein the positionable tissue approximating structure extends through the body wall.

* * * * *

UNITED STATES PATENT AND TRADEMARK OFFICE
CERTIFICATE OF CORRECTION

PATENT NO.        : 8,764,775 B2
APPLICATION NO.   : 10/919775
DATED             : July 1, 2014
INVENTOR(S)       : Copa et al.

Page 1 of 1

It is certified that error appears in the above-identified patent and that said Letters Patent is hereby corrected as shown below:

IN THE SPECIFICATION:

In Column 4, Line 56, delete "illustrates" and insert -- illustrate --, therefor.

In Column 16, Line 2, delete "approximating structure 264" and insert -- approximating structure 266 --, therefor.

In Column 22, Line 61, delete "tines 125" and insert -- tines 122 --, therefor.

Signed and Sealed this
Nineteenth Day of January, 2016

Michelle K. Lee
*Director of the United States Patent and Trademark Office*